United States Patent
Blumenkopf et al.

(10) Patent No.: US 7,101,869 B2
(45) Date of Patent: Sep. 5, 2006

(54) 2,4-DIAMINOPYRIMIDINE COMPOUNDS USEFUL AS IMMUNOSUPPRESSANTS

(75) Inventors: Todd A. Blumenkopf, Old Lyme, CT (US); Eileen Elliott Mueller, Old Lyme, CT (US); Eric Jan Roskamp, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 357 days.

(21) Appl. No.: 10/302,742

(22) Filed: Nov. 22, 2002

(65) Prior Publication Data

US 2003/0191307 A1 Oct. 9, 2003

Related U.S. Application Data

(63) Continuation of application No. 10/116,554, filed on Apr. 4, 2002, now abandoned, which is a continuation of application No. 09/693,993, filed on Oct. 23, 2000, now abandoned.

(60) Provisional application No. 60/168,224, filed on Nov. 30, 1999.

(51) Int. Cl.
  *C07D 401/04* (2006.01)
  *A61K 31/506* (2006.01)

(52) U.S. Cl. .............. 514/211.09; 514/212.07; 514/221; 514/249; 514/252.02; 514/265.1; 514/275; 540/552; 540/567; 540/593; 544/238; 544/280; 544/323; 544/324

(58) Field of Classification Search ........... 544/238, 544/280, 323, 324; 540/552, 567, 593; 514/211.09, 514/221, 212.07, 249, 265.1, 275, 252.02
See application file for complete search history.

(56) References Cited

U.S. PATENT DOCUMENTS

| | | | |
|---|---|---|---|
| 5,304,555 A | 4/1994 | Awaya et al. | |
| 5,358,945 A | 10/1994 | Mizuchi et al. | |

FOREIGN PATENT DOCUMENTS

| | | |
|---|---|---|
| EP | 0489925 | 6/1992 |
| EP | 0837063 | 4/1998 |
| WO | WO9200970 | 1/1992 |
| WO | WO9719065 | 5/1997 |
| WO | WO9740019 | 10/1997 |
| WO | WO9744326 | 11/1997 |
| WO | WO9811095 | 3/1998 |
| WO | WO9818782 | 5/1998 |
| WO | WO9828281 | 7/1998 |
| WO | WO9841525 | 9/1998 |
| WO | WO9854156 | 12/1998 |
| WO | WO9854157 | 12/1998 |
| WO | WO9909845 | 3/1999 |
| WO | WO9910341 | 3/1999 |
| WO | WO9924035 | 5/1999 |
| WO | WO0024744 | 5/2000 |
| WO | WO0053595 | 9/2000 |

OTHER PUBLICATIONS

Johnson et al., Cutaneous T–cell lymphoma, http://www.healthatoz.com/healthatoz/Atoz/ency/cutaneous_t–cell_lymphoma.html, Dec. 2002.*
Damasio, Alzheimer's Disease and Related Dementias, Cecil Textbook of Medicine, 20th Edition, vol. 2, pp. 1992–1996, 1996.*
Rutella et al., PubMed Abstract (Exp Hematol 29(4):401–15), Apr. 2001.*
Irani et al., PubMed Abstract (J Immunol 158(5):2318–26), Mar. 1997.*
Casanova et al., PubMed Abstract (Rev Neurol. 28(9):909–15) May 1999.*
Bremer et al., Therapy of Crohn's Disease in Childhood, Exp Opin Pharmacother, 3(7):809–825, 2002.*
Robinson, Medical Therapy of Inflammatory Bowel Disease for the 21st Century, Eur. J. Surg. Suppl. 582:90–98, 1998.*
Singh et al., Immune Therapy in Inflammatory bowel disease and models of colitis, British Journal of Surgery, 88, 1558–1569, 2001.*

(Continued)

*Primary Examiner*—Deepak Rao
(74) *Attorney, Agent, or Firm*—Peter C. Richardson; Gregg C. Benson; Nicholas J. Sisti

(57) ABSTRACT

Novel compounds according to the formula

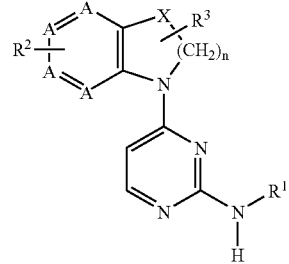

(formula I)

and pharmaceutically acceptable salts, solvates, or hydrates thereof; wherein
each occurrence of A is independently selected from CH or N;
X is selected from the group consisting of —$CH_2$—, —O—, —NH—, ($C_1$–$C_6$)alkylamino-, ($C_1$–$C_6$)alkylaminocarbonylamino-, ($C_1$–$C_6$)alkylcarbonylamino-, ($C_1$–$C_6$)alkylsulfonylamino-, phenylsulfonylamino-, carbonyl, —NH—C(O)—, —N($C_1$–$C_6$)alkyl-C(O)—, —S(O)$_y$— where y is 0, 1 or 2, and;
n in —$(CH_2)_n$— is 1, 2 or 3; and
$R^1$, $R^2$, and $R^3$ are as described herein; pharmaceutical compositions that including these compounds, and methods for the treatment of autoimmune disease, inflammation, allergy, transplant rejection, and other circumstances where administration of an immunosuppressive agent is of therapeutic benefit.

13 Claims, No Drawings

OTHER PUBLICATIONS

Wachlin et al., IL–1beta, IFN–gamma and TNF–alpha increase vulnerability of pancreatic beta cells to autoimmune destruction, Journal of Autoimmunity, 20:303–312, 2003.*

Elgert, Autoimmunity, Immunology: Understanding the Immune System, pp. 315–330, 1996.*

Beers et al., Crohn's Disease and Ulcerative Colitis, The Merck Manual of Diagnosis and Therapy, Seventeenth Edition (Online), 1999.*

Hanke, J. H., et al., *Role of tyrosine kinases in lymphocyte activation: Targets for drug intervention*, Inflamm. Res., vol. 44, pp. 357–371, (1995).

Molina, T. J., et al., *Profound block in thymocyte development in mice lacking p56$^{lck}$*, Nature, vol. 357, May 14, 1992, pp. 161–164.

June, Carl H., et al., *Increases in tyrosine phosphorylation are detectable before phospholipase c activation after T cell receptor stimulation*, Journal of Immunology, vol. 144, pp. 1591–1599, No. 5, Mar. 1, 1990.

Straus, David B., et al., *Genetic evidence for the involvement of the lck tyrosine kinase in signal transduction through the T cell antigen receptor*, Cell, vol. 70, pp. 585–593, Aug. 21, 1992.

June, Carl H., et al., *Inhibition of tyrosine phosphorylation prevents T–cell receptor–mediated signal transduction*, Proc. Natl. Acad. Sci. USA, vol. 87, pp. 7722–7726, Oct. 1990.

English language equivalent of WO 92/00970, 1992.

* cited by examiner

2,4-DIAMINOPYRIMIDINE COMPOUNDS USEFUL AS IMMUNOSUPPRESSANTS

This application is a continuation of Ser. No. 10/116,554 filed Apr. 4, 2002 now abandoned which is a continuation of Ser. No. 09/693,993 filed Oct. 23, 2000 now abandoned which claims the benefit of Provisional Application No. 60/168,224 filed Nov. 30, 1999.

FIELD OF THE INVENTION

The present invention relates to therapeutic modulation of T-cell mediated cellular processes. T-cells ("thymus-derived" cells) are responsible for numerous cell-mediated immune functions, and indirectly, by stimulating B-cells, contribute to antibody production. The cell membrane of a T-cell contains numerous receptor and accessory protein molecules that facilitate activation of T-cells, differentiation of T-cells into various subtypes, and the interaction of T-cells with other cells or cell components.

Although T-cell mediated immune,responses are normally of great benefit, there are circumstances where it is appropriate to suppress or otherwise modulate immune response mediated by activated T-cells. An important example is organ, tissue, or cell transplantation, where suppression of immune response against the transplant (whether allograft or xenograft) is essential. Additional examples include treatment of allergy, autoimmune disease, and disease states involving inflammation. Since T-cells are involved in so many immune-mediated processes, and such processes generally involve overlapping use of various T-cell proteins and signaling functions, it has been very difficult to modulate only certain T-cell functions, without adversely affecting other desirable cellular processes. The present invention is directed to a class of therapeutic compounds that selectively interfere with certain signaling events that occur during T-cell activation, thus permitting selective regulation of immune response.

REPORTED DEVELOPMENTS

T-cells differentiate and proliferate in response to recognition of antigens (generally, foreign macromolecules) in order to carry out various cell-mediated immune processes. This recognition of antigen, followed by functional and morphological changes in the T-cell, is termed activation. Among the functions carried out by differentiated T-cells are (1) killing of virus-infected self cells, (2) killing foreign cells, (3) activation of other cells (for example, macrophages) that are capable of engulfing foreign particles (such as bacteria and viruses), and in turn processing their macromolecules for presentation to, and activation of, additional T-cells, (4) suppression of immune response of B-cells and T-cells to antigen, which, for example, may act to establish immune tolerance, (5) activation of other T-cells, and (6) once themselves activated by antigen, helping B-cells respond to foreign antigens so that antibodies can be produced. In some cases these effects are carried out by direct contact of T-cells with their targets, and in other cases T-cells secrete a variety of substances (generically termed lymphokines) in order to activate target cells at a distance, or both mechanisms may be involved.

As aforementioned, autoimmune disease, transplant rejection, allergy, and inflammation represent disease states wherein undesired activation of antigen-specific T-cells appears necessary for induction and/or progression of the unwanted clinical state. For example, necessary release of some lymphokines (such as γ-interferon) by T-cells may cause macrophage cells to not only migrate to a site of infection or tissue damage, but to release other soluble factors that slowly trigger undesired inflammation (for example, in delayed type hypersensitivity). Accordingly, pharmaceutical compounds that interrupt activation of T-cells under specific circumstances, or specific downstream signalling events, are expected to be of great therapeutic value. See, for example, J. H. Hanke, et al., *Inflammation Research*, 44, pp. 357–371, 1995.

T-cells recognize antigen through membrane glycoprotein receptors, called TcR, which are, in part, similar in structure and sequence to the antibodies of B-cells. The genetic elements from which the two protein classes are expressed are undoubtedly of common origin. In general, T-cells only recognize antigen that is presented to them, in processed form, on the surface of other cells. Like antibody producing B-cells, each individual progenitor T-cell only recognizes a particular amino acid or carbohydrate sequence and/or other molecular structure (termed an epitope) in the processed antigen, which structure is usually unique to the antigen. Such specific recognition of antigen permits response against a wide range of foreign macromolecules, and is a necessary feature of mechanisms whereby immune responses against self-molecules are normally prevented.

Following the binding of antigen to the T-cell surface, numerous events must occur in the cell membrane and inside the T-cell to complete its activation. As reviewed in Hanke et al., activation of the T-cell involves association of other cell membane glycoproteins, such as among CD4, CD8, CD3 and CD28, with the TcR, and also phosphorylation of tyrosine amino acid residues in these proteins (see C. H. June et al., *Journal of Immunology*, 144, pp. 1591–1599 (1990), and D. B. Strauss et al., *Cell*, 70, pp. 585–593, 1992). Phosphorylation of tyrosine amino acid residues is carried out by a class of enzymes known as protein tyrosine kinases (PTKs). Inhibition of phosphorylation by tyrosine kinases has been shown to modulate T-cell activation, and numerous T-cell mediated immune processes. (see, for example, C. H. June et al., *Proceedings of the National Academy of Sciences, USA*, 87, pp. 7722–7726, 1990). Accordingly, regulation of T-cell activation (or subsequent signal transducting events) by selective inhibition of particular PTKs has been of particular interest.

However, phosphorylation of tyrosine resides in membrane bound and cytoplasmic proteins is a general mechanism. It plays an important role in numerous signaling pathways, not merely those confined to the immune system. Tyrosine phosphorylation occurs, for example, in response to binding of growth factors such as epidermal growth factor (EGF), platelet-derived growth factor(PDGF), nerve growth factor (NGF), and also insulin. Given the presence of a large number of cellular processes dependent upon tyrosine phosphorylation, it will be immediately apparent that preferred compounds for inhibition of T-cell activation, and/or subsequent immune system signalling events, should be designed to inhibit only one (or at most a very few) tyrosine kinases, to thus avoid interfering with a wide range of other cellular metabolic pathways.

Additionally, since the specificity of a particular inhibitor compound cannot be practically tested against all tyrosine kinases, and indeed numerous kinases remain to be discovered, it is most preferred to provide compounds that are highly specific for a particular tyrosine kinase. A general discussion of tyrosine kinase proteins known to be associated with T-cell activation is provided in J. H. Hanke et al., 1995. Tyrosine kinases (PTKs) involved in regulation of T-cell activation include:

(a) lck (a 56,000 MW protein, also known as p56$^{lck}$) which is associated with the TcR complex, and which is in the src-kinase family;

(b) fyn which is also in the src-kinase family;

(c) Zap-70 and syk, which share limited homology with src-kinases;

(d) itk kinase, which may be associated with the CD28 receptor; and (e) csk-like kinases, and which may also negatively regulate the function of other PTKs.

Considerable evidence supports the involvement of lck in T-cell activation, and suggests that inhibition of lck activity is an important point of therapeutic intervention. D. B. Strauss et al., 1992, determined that mutant Jurkat cells (JcaM1) that failed to show an increase in calcium levels following receptor stimulation lacked expression of functional lck tyrosine kinase. T. J. Molina et al., *Nature,* 357, pp. 161–164, 1992 generated an lck null mutation by homologous recombination in murine embryonic stem cells. Lck-deficient mice evidenced pronounced thymic atrophy, and few CD4+, CD8+, or CD4+/CD8+ thymocytes were detected. Additionally, F. D. Goldman et al., *Journal of Clinical Investigation,* 102, pp. 421–429, 1998, have reported on an infant patient presenting a SCID (severe combined immune deficiency) phenotype in which p59fyn and ZAP-70 kinases were expressed at normal levels, although a marked decrease in the level of lck was noted. Interestingly, an alternatively spliced lck transcript, that lacked the kinase-encoding domain provided by exon 7 of the lck gene, was identified from the patient.

There are reports in the scientific literature of compounds that modulate T-cell mediated immune function, and/or which inhibit tyrosine kinases (PTKs) of the receptor and non-receptor type. For example, published international patent documents WO 98/54156 and WO 98/54157 describe quinoline and quinoxaline compounds that inhibit platelet-derived growth factor PTK and/or lck, and are useful in affecting T-cell activation and proliferation. Additionally WO 97/40019 discloses 5-aminopyrazole compounds useful as selective inhibitors of lck. The disclosure in WO 98/11095 recites substituted 2-pyrimidineamines, and their use as inhibitors of protein kinases such as ZAP-70, protein kinase C and lck. The compounds are described as useful in regard to diseases or conditions involving the immune system or cellular hyperproliferation. Additional publications of note include WO 99/24035, WO 98/41525, WO 97/19065, WO 98/28281 and WO 98/18782.

The present invention provides pharmaceutical compounds useful for the treatment of clinical conditions that involve inappropriate T-cell activation. In particular, highly specific inhibitors of lck tyrosine kinase are disclosed.

SUMMARY OF THE INVENTION

Accordingly, there are provided compounds according to the formula

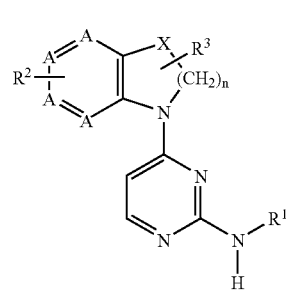

(formula I)

or pharmaceutically acceptable salts, solvates, or hydrates thereof; wherein each occurrence of A is independently selected from CH or N;

X is selected from the group consisting of —$CH_2$—, —O—, —NH—, ($C_1$–$C_6$)alkylamino-, ($C_1$–$C_6$) alkylaminocarbonylamino-, ($C_1$–$C_6$)alkylcarbonylamino-, ($C_1$–$C_6$)alkylsulfonylamino-, phenylsulfonylamino-, carbonyl, —NH—C(O)—, —N($C_1$–$C_6$)alkyl-C(O)—, —S(O)$_y$— where y is 0, 1 or 2, and;

n in —$(CH_2)_n$— is 1, 2 or 3;

$R^1$ is selected from the groups consisting of ($C_6$–$C_{10}$) aryl-, ($C_1$–$C_9$)heteroaryl-, ($C_6$–$C_{10}$)aryl($C_6$–$C_{10}$)aryl-, ($C_6$–$C_{10}$)aryl($C_1$–$C_9$)heteroaryl-, ($C_1$–$C_9$)heteroaryl($C_1$–$C_9$) heteroaryl-, ($C_1$–$C_9$)heteroaryl($C_6$–$C_{10}$)aryl-, ($C_6$–$C_{10}$) arylsulfinyl-, ($C_6$–$C_{10}$)aryl($C_6$–$C_{10}$)arylsulfinyl-, ($C_1$–$C_9$) heteroaryl($C_6$–$C_{10}$)arylsulfinyl-, ($C_6$–$C_{10}$)arylsulfonyl-, ($C_6$–$C_{10}$)aryl($C_6$–$C_{10}$)arylsulfonyl-, ($C_1$–$C_9$)heteroaryl ($C_6$–$C_{10}$)arylsulfonyl-, ($C_1$–$C_9$)heteroarylsulfinyl-, ($C_1$–$C_9$) heteroaryl($C_1$–$C_9$)heteroarylsulfinyl-, ($C_6$–$C_{10}$)aryl($C_1$–$C_9$) heteroarylsulfinyl-, ($C_1$–$C_9$)heteroarylsulfonyl-, ($C_1$–$C_9$) heteroaryl($C_1$–$C_9$)heteroarylsulfonyl-, ($C_6$–$C_{10}$)aryl($C_1$–$C_9$) heteroarylsulfonyl-, ($R^4$)sulfinyl-, ($R^4$)sulfonyl-, ($C_6$–$C_{10}$) aryl($R^4$)sulfinyl-, ($C_6$–$C_{10}$)aryl($C_6$–$C_{10}$)aryl($R^4$)sulfinyl-, ($C_1$–$C_9$)heteroaryl($C_6$–$C_{10}$)aryl($R^4$)sulfinyl-, ($C_6$–$C_{10}$)aryl ($R^4$)sulfonyl-, ($C_6$–$C_{10}$)aryl($C_6$–$C_{10}$)aryl($R^4$)sulfonyl-, ($C_1$–$C_9$)heteroaryl($C_6$–$C_{10}$)aryl($R^4$)sulfonyl-, ($C_1$–$C_9$) heteroaryl($R^4$)sulfinyl-, ($C_6$–$C_{10}$)aryl($C_1$–$C_9$)heteroaryl($R^4$) sulfinyl-, ($C_1$–$C_9$)heteroaryl($C_1$–$C_9$)heteroaryl($R^4$)sulfinyl-, ($C_1$–$C_9$)heteroaryl($R^4$)sulfonyl-, ($C_6$–$C_{10}$)aryl($C_1$–$C_9$) heteroaryl($R^4$)sulfonyl-, ($C_1$–$C_9$)heteroaryl($C_1$–$C_9$) heteroaryl($R^4$)sulfonyl-, ($C_6$–$C_{10}$)arylaminocarbonyl-, ($C_6$–$C_{10}$)aryl($C_6$–$C_{10}$)arylaminocarbonyl-, ($C_1$–$C_9$) heteroaryl($C_6$–$C_{10}$)arylaminocarbonyl-, ($C_1$–$C_9$) heteroarylaminocarbonyl-, ($C_6$–$C_{10}$)aryl($C_1$–$C_9$) heteroarylaminocarbonyl-, ($C_1$–$C_9$)heteroaryl($C_1$–$C_9$) heteroarylaminocarbonyl-, ($C_6$–$C_{10}$)arylcarbonyl-, ($C_6$–$C_{10}$) aryl($C_6$–$C_{10}$)arylcarbonyl-, ($C_1$–$C_9$)heteroaryl($C_6$–$C_{10}$) arylcarbonyl-, ($C_1$–$C_9$)heteroarylcarbonyl-, ($C_6$–$C_{10}$)aryl ($C_1$–$C_9$)heteroarylcarbonyl-($C_1$–$C_9$)heteroaryl($C_1$–$C_9$) heteroarylcarbonyl-, ($C_6$–$C_{10}$)aryloxycarbonyl-, ($C_6$–$C_{10}$) aryl($C_6$–$C_{10}$)aryloxycarbonyl-, ($C_1$–$C_9$)heteroaryl($C_6$–$C_{10}$) aryloxycarbonyl-, ($C_1$–$C_9$)heteroaryloxycarbonyl-, ($C_6$–$C_{10}$)aryl($C_1$–$C_9$)heteroaryloxycarbonyl-, ($C_1$–$C_9$) heteroaryl($C_1$–$C_9$)heteroaryloxycarbonyl-, ($R^4$)carbonyl-, ($R^4$)oxycarbonyl-, ($R^4$)aminocarbonyl-, ($C_6$–$C_{10}$)aryl($R^4$) carbonyl-, ($C_6$–$C_{10}$)aryl($R^4$)oxycarbonyl-, ($C_6$–$C_{10}$)aryl($R^4$) aminocarbonyl-, ($C_1$–$C_9$)heteroaryl($R^4$)carbonyl-, ($C_1$–$C_9$) heteroaryl($R^4$)oxycarbonyl-, and ($C_1$–$C_9$)heteroaryl($R^4$) aminocarbonyl-;

wherein $R^4$ is selected from the groups consisting of (a) ($C_1$–$C_6$)alkyl-, ($C_2$–$C_6$)alkenyl-, or ($C_2$–$C_6$)alkynyl-, wherein the alkyl-, alkenyl- and alkynyl- groups are optionally substituted by hydroxy, halo, amino, trifluoromethyl, hydroxy($C_2$–$C_6$)alkyl-, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl(difluoromethylene)($C_1$–$C_3$)alkyl-, or nitro($C_1$–$C_6$)alkyl-;

(b) ($C_3$–$C_{10}$)cycloalkyl-, wherein the cycloalkyl- group is optionally substituted by hydroxy, halo, amino, trifluoromethyl, hydroxy($C_2$–$C_6$)alkyl-, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl(difluoromethylene)($C_1$–$C_3$)alkyl-, or nitro($C_1$–$C_6$)alkyl-; or (c) ($C_3$–$C_{10}$)heterocycloalkyl-, wherein the heterocycloalkyl- group is optionally substituted by hydroxy, halo, amino, trifluoromethyl, hydroxy($C_2$–$C_6$)alkyl-, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl(difluoromethylene)($C_1$–$C_3$)alkyl-, or nitro($C_1$–$C_6$)alkyl-; and wherein any of said of ($C_6$–$C_{10}$)aryl- or ($C_1$–$C_9$)heteroaryl- groups of $R^1$ may be optionally substituted by one to five groups selected from (a) deuterium, hydroxy, halo, amino, trifluoromethyl, carboxy, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$$C_6$)alkynyl-, ($C_1$–$C_6$)acylamino-, cyano($C_1$–$C_6$)alkyl-, trifluoromethyl($C_1$–$C_6$)alkyl-, or nitro($C_1$–$C_6$)alkyl-, ($C_1$–$C_3$)alkyl(difluoromethylene)($C_1$–$C_3$)alkyl-, ($C_1$–$C_6$)acylamino($C_1$–$C_6$)alkyl-, ($C_1$–$C_6$)alkoxy($C_1$–$C_6$)acylamino-, amino($C_1$–$C_6$)acyl-, amino($C_1$–$C_6$)acyl($C_1$–$C_6$)alkyl-, ($C_1$–$C_6$)alkylamino($C_1$–$C_6$)acyl-, (($C_1$–$C_6$)alkyl)$_2$amino($C_1$–$C_6$)acyl-, ($C_3$–$C_{10}$)cycloalkyl($C_1$–$C_6$)alkyl-, ($C_1$–$C_6$)acyloxy($C_1$–$C_6$)alkyl-, ($C_2$–$C_6$)alkoxy($C_1$–$C_6$)alkyl-, piperazinyl($C_1$–$C_6$)alkyl-, ($C_1$–$C_6$)acylamino($C_1$–$C_6$)alkyl-, ($C_6$–$C_{10}$)aryl($C_1$–$C_6$)alkoxy($C_1$–$C_6$)alkyl-, ($C_5$–$C_9$)heteroaryl($C_1$–$C_6$)alkoxy($C_1$–$C_6$)alkyl-, ($C_1$–$C_6$)alkylthio($C_1$–$C_6$)alkyl-, ($C_6$–$C_{10}$)arylthio($C_1$–$C_6$)alkyl-, ($C_1$–$C_6$)alkylsulfinyl($C_1$–$C_6$)alkyl-, ($C_6$–$C_{10}$)arylsulfinyl($C_1$–$C_6$)alkyl-, ($C_1$–$C_6$)alkylsulfonyl($C_1$–$C_6$)alkyl-, ($C_6$–$C_{10}$)arylsulfonyl($C_1$–$C_6$)alkyl-, amino($C_1$–$C_6$)alkyl-, ($C_1$–$C_6$)alkylamino($C_1$–$C_6$)alkyl-, ($C_1$–$C_6$)alkyl(difluoromethylene)-, ($C_1$–$C_3$)alkyl(difluoromethylene)($C_1$–$C_3$)alkyl-, ($C_1$–$C_6$)alkoxy($C_1$–$C_6$)acyl-, ($C_1$–$C_6$)alkylamino($C_1$–$C_6$)acyl-, (($C_1$–$C_6$)alkyl)$_2$amino($C_1$–$C_6$)acyl-, ($C_6$–$C_{10}$)aryl-, ($C_1$–$C_9$)heteroaryl-, ($C_6$–$C_{10}$)aryl($C_1$–$C_6$)alkyl-, ($C_1$–$C_9$)heteroaryl($C_1$–$C_6$)alkyl-, ($C_6$–$C_{10}$)aryl($C_6$–$C_{10}$)aryl-, ($C_6$–$C_{10}$)aryl($C_6$–$C_{10}$)aryl($C_1$–$C_6$)alkyl-, ($C_3$–$C_{10}$)cycloalkyl-, ($C_3$–$C_6$)cycloalkyl($C_1$–$C_6$)alkyl-, ($C_3$–$C_{10}$)heterocycloalkyl-, ($C_3$–$C_{10}$)heterocycloalkyl($C_1$–$C_6$)alkyl-, hydroxy($C_2$–$C_6$)alkyl-, ($C_1$–$C_6$)acyloxy($C_2$–$C_6$)alkyl-, ($C_1$–$C_6$)alkoxy($C_2$–$C_6$)alkyl-, piperazinyl($C_1$–$C_6$)alkyl-, ($C_1$–$C_6$)acylamino($C_1$–$C_6$)alkyl-, ($C_6$–$C_{10}$)aryl($C_1$–$C_6$)alkoxy($C_1$–$C_6$)alkyl-, ($C_1$–$C_9$)heteroaryl($C_1$–$C_6$)alkoxy($C_1$–$C_6$)alkyl-, ($C_1$–$C_6$)alkylthio($C_1$–$C_6$)alkyl-, ($C_6$–$C_{10}$)arylthio($C_1$–$C_6$)alkyl-, ($C_1$–$C_6$)alkylsulfinyl($C_1$–$C_6$)alkyl-, ($C_6$–$C_{10}$)arylsulfinyl($C_1$–$C_6$)alkyl-, ($C_1$–$C_6$)alkylsulfonyl($C_1$–$C_6$)alkyl-, ($C_6$–$C_{10}$)arylsulfonyl($C_1$–$C_6$)alkyl-, amino($C_1$–$C_6$)alkyl-, ($C_1$–$C_6$)alkylamino($C_1$–$C_6$)alkyl-, (($C_1$–$C_6$)alkyl)$_2$amino($C_1$–$C_6$)alkyl-;

(b) $R^5$OCO($C_1$–$C_6$)alkyl-, wherein $R^5$ is selected from the group consisting of hydrogen, ($C_1C_6$)alkyl-, ($C_6$–$C_{10}$)aryl($C_1$–$C_6$)alkyl-, ($C_1$–$C_9$)heteroaryl($C_1$–$C_6$)alkyl-; or (c) $R^6$($C_0$–$C_6$)alkyl-, wherein $R^6$ is selected from the group consisting of piperazino, ($C_1$–$C_6$)acylpiperazino-, ($C_6$–$C_{10}$)arylpiperazino-, ($C_5$–$C_9$)heteroarylpiperazino-, ($C_1$–$C_6$)alkylpiperazino-, ($C_6$–$C_{10}$)aryl($C_1$–$C_6$)alkylpiperazino-, ($C_1$–$C_9$)heteroaryl($C_1$–$C_6$)alkylpiperazino-, morpholino-, ($C_1$–$C_6$)acylmorpholino-, ($C_6$–$C_{10}$)arylmorpholino-, ($C_1$–$C_9$)heteroarylmorpholino-, ($C_1$–$C_6$)alkylmorpholino-, ($C_6$–$C_{10}$)aryl($C_1$–$C_6$)alkylmorpholino-, ($C_1$–$C_9$)heteroaryl($C_1$–$C_6$)alkylmorpholino-, thiomorpholino-, ($C_1$–$C_6$)acylthiomorpholino-, ($C_6$–$C_{10}$)arylthiomorpholino-, ($C_1$–$C_9$)heteroarylthiomorpholino-, ($C_1$–$C_6$)alkylthiomorpholino-, ($C_6$–$C_{10}$)aryl($C_1$–$C_6$)alkylthiomorpholino-, ($C_1$–$C_9$)heteroaryl($C_1$–$C_6$)alkylthiomorpholino-, piperidino-, ($C_1$–$C_6$)acylpiperidino-, ($C_6$–$C_{10}$)arylpiperidino-, ($C_1$–$C_9$)heteroarylpiperidino-, ($C_1$–$C_6$)alkyl piperidino-, ($C_6$–$C_{10}$)aryl($C_1$–$C_6$)piperidino-, ($C_1$–$C_9$)heteroaryl($C_1$–$C_6$)alkylpiperidino-, pyrrolidino-, ($C_1$–$C_6$)acylpyrrolidino-, ($C_6$–$C_{10}$)aryl-pyrrolidino-, ($C_1$–$C_9$)heteroaryl-pyrrolidino-, ($C_1$–$C_6$)alkylpyrrolidino-, ($C_6$–$C_{10}$)aryl($C_1$–$C_6$)pyrrolidino-, ($C_1$–$C_9$)heteroaryl($C_1$–$C_6$)alkylpyrrolidino-, ($C_1$–$C_6$)alkoxy($C_1$–$C_6$)acyl-, ($C_1$–$C_6$)alkylamino($C_6$–$C_{10}$)aryl-, and ((($C_1$–$C_6$)alkyl)$_2$amino ($C_1$–$C_6$)acyl-;

$R^2$ represents one to four optional substituents, each being independently selected from the members of groups (a) to (f)

(a) deuterium, halo, hydroxy, carboxy, amino, trifluoromethyl, ($C_1$–$C_6$)alkyl-, ($C_2$–$C_6$)alkenyl-, ($C_2C_6$)alkynyl-, ($C_1$–$C_6$)alkylamino-, (($C_1$–$C_6$)(alkyl)$_2$amino-, cyanoalkyl-, ($C_3$–$C_{10}$)cycloalkyl-, ($C_3$–$C_{10}$)heterocycloalkyl-, ($C_3$–$C_{10}$)cycloalkoxy-, ($C_1$–$C_6$)alkylthio-, ($C_1$–$C_6$)alkylsulfinyl-, ($C_1$–$C_6$)alkylsulfonyl-, amino-CO—NH—, ($C_1$–$C_6$)alkoxy-CO—NH—, ($C_1$–$C_6$)alkyl-CO—NH—, ($C_1$–$C_6$)alkyl-CO—NH—($C_1$–$C_6$)alkyl-, ($C_1$–$C_6$)alkyl-CO—NH—($C_1$–$C_6$)alkoxy-, ($C_1$–$C_6$)alkoxycarbonyl($C_1$–$C_6$)alkoxy-, ($C_1$–$C_6$)alkoxy-CO—NH—($C_1$–$C_6$)alkoxy-, ($C_1$–$C_6$)alkylamino-CO—NH—, ($C_1$–$C_6$)alkylamino-CO—NH—($C_1$–$C_6$)alkyl-, (($C_1$–$C_6$)alkyl)$_2$amino-CO—NH—($C_1$–$C_6$)alkyl-, (($C_1$–$C_6$)alkyl)$_2$amino-CO—NH-carboxy, carboxy($C_1$–$C_6$)alkyl-, carboxy ($C_1$–$C_6$)alkoxy-, benzyloxycarbonyl($C_1$–$C_6$)alkoxy-, ($C_1$–$C_6$)alkylamino-CO—, ($C_1$–$C_6$)acylamino-, ($C_1$–$C_6$)alkoxy-, ($C_1$–$C_6$)acyl-, ($C_1$–$C_6$)acyloxy-, ($C_1$–$C_6$)acyl($C_1$–$C_6$)alkylamino-, ($C_1$–$C_6$)alkoxyacyl-, ($C_1$–$C_6$)alkylaminoacyl-, (($C_1$–$C_6$)alkyl)$_2$aminoacyl-, amino ($C_1$–$C_6$)acyl-, amino($C_1$–$C_6$)alkyl-, ($C_1$–$C_6$)alkoxycarbonylamino-, ($C_1$–$C_6$)alkoxycarbonyl($C_1$–$C_6$)alkyl-, ($C_6$–$C_{10}$)aryl($C_1$–$C_6$)alkoxycarbonylamino-, trihalomethyl-, trihalomethyl($C_1$–$C_6$)alkyl-, ($C_1$–$C_6$)alkyldihalomethylene-, ($C_1$–$C_3$)alkyl(dihalomethylene)($C_1$–$C_3$)alkyl-, ($C_3$–$C_6$)cycloalkyl-, ($C_3$–$C_6$)cycloalkyl($C_1$–$C_6$)alkyl-, hydroxy($C_1$–$C_6$)alkyl-, ($C_1$–$C_6$)acyloxy($C_1$–$C_6$)alkyl-, ($C_1$–$C_6$)alkoxy($C_1$–$C_6$)alkyl-, ($C_1$–$C_6$)acylamino($C_1$–$C_6$)alkyl-, ($C_1$–$C_6$)alkylthio($C_1$–$C_6$)alkyl-, ($C_1$–$C_6$)alkoxycarbonyl-, ($C_1$–$C_6$)alkylsulfinyl($C_1$–$C_6$)alkyl-, ($C_1$–$C_6$)alkylsulfonyl($C_1$–$C_6$)alkyl-, ($C_1$–$C_6$)alkylsulfonyl-, ($C_1$–$C_6$)alkylsulfonylamino-, ($C_1$–$C_6$)alkylsulfonylamino($C_1$–$C_6$)alkyl-, amino($C_1$–$C_6$)alkyl-, ($C_1$–$C_6$)alkylamino($C_1$–$C_6$)alkyl-, (($C_1$–$C_6$)alkyl)$_2$amino ($C_1$–$C_6$)alkyl-, ($C_1$–$C_6$)CO($C_1$–$C_6$)alkyl-;

(b) ($C_6$–$C_{10}$)aryl-, ($C_1$–$C_9$)heteroaryl-, ($C_6$–$C_{10}$)aryl($C_6$–$C_{10}$)aryl-, ($C_6$–$C_{10}$)aryl($C_1$–$C_9$)heteroaryl-, ($C_1$–$C_9$)heteroaryl($C_1$–$C_9$)heteroaryl-, ($C_1$–$C_9$)heteroaryl($C_6$–$C_{10}$)aryl-, ($C_6$–$C_{10}$)arylsulfinyl-, ($C_6$–$C_{10}$)aryl($C_6$–$C_{10}$)arylsulfinyl-, ($C_1$–$C_9$)heteroaryl($C_6$–$C_{10}$)arylsulfinyl-, ($C_6$–$C_{10}$)arylsulfonyl-, ($C_6$–$C_{10}$)aryl($C_6$–$C_{10}$)arylsulfonyl-, ($C_1$–$C_9$)heteroaryl($C_6$–$C_{10}$)arylsulfonyl-, ($C_1$–$C_9$)

heteroarylsulfinyl-, $(C_1-C_9)$heteroaryl$(C_1-C_9)$ heteroarylsulfinyl-, $(C_6-C_{10})$aryl$(C_1-C_9)$heteroarylsulfinyl-, $(C_1-C_9)$heteroarylsulfonyl-, $(C_6-C_{10})$aryl$(C_1-C_9)$ heteroarylsulfonyl-, $(R^4)$sulfinyl-, $(R^4)$sulfonyl-, $(C_6-C_{10})$ aryl$(R^4)$sulfinyl-, $(C_6-C_{10})$aryl$(R^4)$sulfinyl-, $(C_6-C_{10})$aryl $(C_6-C_{10})$aryl$(R^4)$sulfinyl-, $(C_1-C_9)$heteroaryl$(C_6-C_{10})$aryl $(R^4)$sulfinyl-, $(C_6-C_{10})$aryl$(R^4)$sulfonyl-, $(C_6-C_{10})$aryl $(C_6-C_{10})$aryl$(R^4)$sulfonyl-, $(C_1-C_9)$heteroaryl$(C_6-C_{10})$aryl $(R^4)$sulfonyl-, $(C_1-C_9)$heteroaryl$(R^4)$sulfinyl-, $(C_6-C_{10})$aryl $(C_1-C_9)$heteroaryl$(R^4)$sulfinyl-, $(C_1-C_9)$heteroaryl$(C_1-C_9)$ heteroaryl$(R^4)$sulfinyl-, $(C_1-C_9)$heteroaryl$(R^4)$sulfonyl-, $(C_6-C_{10})$aryl$(C_5-C_9)$heteroaryl$(R^4)$sulfonyl-, $(C_1-C_9)$ heteroaryl$(C_1-C_9)$heteroaryl$(R^4)$sulfonyl-, $(C_6-C_{10})$ arylaminocarbonyl-, $(C_6-C_{10})$aryl$(C_6-C_{10})$ arylaminocarbonyl-, $(C_1-C_9)$heteroaryl$(C_6-C_{10})$ arylaminocarbonyl-, $(C_1-C_9)$heteroarylaminocarbonyl-, $(C_6-C_{10})$aryl$(C_1-C_9)$heteroarylaminocarbonyl-, $(C_1-C_9)$ heteroaryl$(C_1-C_9)$heteroarylaminocarbonyl-, $(C_6-C_{10})$ arylcarbonyl-, $(C_8-C_{10})$aryl$(C_8-C_{10})$arylcarbonyl-, $(C_1-C_9)$ heteroaryl$(C_6-C_{10})$arylcarbonyl-, $(C_1-C_9)$ heteroarylcarbonyl-, $(C_6-C_{10})$aryl$(C_1-C_9)$ heteroarylcarbonyl-, $(C_1-C_9)$heteroaryl$(C_1-C_9)$ heteroarylcarbonyl-, $(C_6-C_{10})$aryloxycarbonyl-, $(C_6-C_{10})$ aryl$(C_6-C_{10})$aryloxycarbonyl-, $(C_1-C_9)$heteroaryl$(C_6-C_{10})$ aryloxycarbonyl-, $(C_1-C_9)$heteroaryloxycarbonyl-, $(C_6-C_{10})$aryl$(C_1-C_9)$heteroaryloxycarbonyl-, $(C_1-C_9)$ heteroaryl$(C_1-C_9)$heteroaryloxycarbonyl-, $(R^4)$carbonyl-, $(R^4)$oxycarbonyl-, $(R^4)$aminocarbonyl-, $(C_6-C_{10})$aryl$(R^4)$ carbonyl-, $(C_6-C_{10})$aryl$(R^4)$oxycarbonyl-, $(C_6-C_{10})$aryl$(R^4)$ aminocarbonyl-, $(C_1-C_9)$heteroaryl$(R^4)$carbonyl-, $(C_5-C_9)$ heteroaryl$(R^4)$oxycarbonyl-, $(C_1-C_9)$heteroaryl$(R^4)$ aminocarbonyl-, wherein $R^4$ is defined as above, and wherein any of said of $(C_6-C_{10})$aryl- or $(C_1-C_9)$heteroaryl-$R^2$ groups may be optionally substituted by one to five groups independently selected from:

(i) hydroxy, halo, amino, trifluoromethyl, carboxy, $(C_1-C_6)$alkoxy-, $(C_1-C_6)$acyloxy-, $(C_1-C_6)$ alkylamino-, $((C_1-C_6)$alkyl$)_2$amino-, $(C_1-C_6)$ acylamino-, cyano, nitro, $(C_1-C_6)$alkyl-, $(C_2-C_6)$ alkenyl-, $(C_2-C_6)$alkynyl-, $(C_1-C_6)$acylamino-, cyano $(C_1-C_6)$alkyl-, trifluoromethyl$(C_1-C_6)$alkyl-, or nitro $(C_1-C_6)$alkyl-, $(C_1-C_3)$alkyl(difluoromethylene) $(C_1-C_3)$alkyl-, $(C_1-C_6)$acylamino$(C_1-C_6)$alkyl-, $(C_1-C_6)$alkoxy$(C_1-C_6)$acylamino-, amino$(C_1-C_6)$ acyl-, amino$(C_1-C_6)$acyl$(C_1-C_6)$alkyl-, $(C_1-C_6)$ alkylamino$(C_1-C_6)$acyl-, $((C_1-C_6)$alkyl$)_2$amino $(C_1-C_6)$acyl-, $(C_3-C_{10})$cycloalkyl$(C_1-C_6)$alkyl-, $(C_1-C_6)$acyloxy$(C_1-C_6)$alkyl-, $(C_2-C_6)$alkoxy$(C_1-C_6)$ alkyl-, piperazinyl$(C_1-C_6)$alkyl-, $(C_1-C_6)$acylamino $(C_1-C_6)$alkyl-, $(C_6-C_{10})$aryl$(C_1-C_6)$alkoxy$(C_1-C_6)$ alkyl-, $(C_1-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio $(C_1-C_6)$alkyl-, $(C_1-C_6)$alkylsulfinyl$(C_1-C_6)$alkyl-, $(C_6-C_{10})$arylsulfinyl$(C_1-C_6)$alkyl-, $(C_1-C_5)$ alkylsulfonyl$(C_1-C_6)$alkyl-, $(C_6-C_{10})$arylsulfonyl $(C_1-C_6)$alkyl-, amino$(C_1-C_6)$alkyl-, $(C_1-C_6)$ alkylamino$(C_1-C_6)$alkyl-, $(C_1-C_6)$alkyl (difluoromethylene)-, $(C_1-C_3)$alkyl (difluoromethylene)$(C_1-C_3)$alkyl-, $(C_1-C_6)$alkoxy $(C_1-C_6)$acyl-, $(C_1-C_6)$alkylamino$(C_1-C_6)$acyl-, $((C_1-C_6)$alkyl$)_2$amino$(C_1-C_6)$acyl-, $(C_6-C_{10})$aryl-, $(C_1-C_9)$heteroaryl-, $(C_6-C_{10})$aryl$(C_1-C_6)$alkyl-, $(C_1-C_9)$heteroaryl$(C_1-C_6)$alkyl-, $(C_6-C_{10})$aryl $(C_6-C_{10})$aryl-, $(C_6-C_{10})$aryl$(C_6-C_{10})$aryl$(C_1-C_6)$ alkyl-, $(C_3-C_{10})$cycloalkyl-, $(C_3-C_6)$cycloalkyl $(C_1-C_6)$alkyl-, $(C_3-C_{10})$heterocycloalkyl-, $(C_3-C_{10})$ heterocycloalkyl$(C_1-C_6)$alkyl-, hydroxy$(C_2-C_6)$alkyl-, $(C_1-C_6)$acyloxy$(C_2-C_6)$alkyl-, $(C_1-C_6)$alkoxy$(C_2-C_6)$ alkyl-, piperazinyl$(C_1-C_6)$alkyl-, $(C_1-C_6)$acylamino $(C_1-C_6)$alkyl-, $(C_6-C_{10})$aryl$(C_1-C_6)$alkoxy$(C_1-C_6)$ alkyl-, $(C_1-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio $(C_1-C_6)$alkyl-, $(C_1-C_6)$alkylsulfinyl$(C_1-C_6)$alkyl-, $(C_6-C_{10})$arylsulfinyl$(C_1-C_6)$alkyl-, $(C_1-C_6)$ alkylsulfonyl$(C_1-C_6)$alkyl-, $(C_6-C_{10})$arylsulfonyl $(C_1-C_6)$alkyl-, amino$(C_1-C_6)$alkyl-, $(C_1-C_6)$ alkylamino$(C_1-C_6)$alkyl-, $((C_1-C_6)$alkyl$)_2$amino $(C_1-C_6)$alkyl-;

(ii) $R^5OCO(C_1-C_6)$alkyl—wherein $R^5$ is selected from the group consisting of hydrogen, $(C_1-C_6)$alkyl, $(C_6-C_{10})$aryl$(C_1-C_6)$alkyl-, $(C_1-C_9)$heteroaryl$(C_1-C_6)$ alkyl-;

(iii) $R^6(C_2-C_6)$alkyl—wherein $R^6$ is selected from the group consisting of piperazino, $(C_1-C_6)$ acylpiperazino-, $(C_6-C_{10})$arylpiperazino-, $(C_5-C_9)$ heteroarylpiperazino-, $(C_1-C_6)$alkylpiperazino-, $(C_6-C_{10})$aryl$(C_1-C_6)$alkylpiperazino-, $(C_1-C_9)$ heteroaryl$(C_1-C_6)$alkylpiperazino-, morpholino-, $(C_1-C_6)$acylmorpholino-, $(C_6-C_{10})$arylmorpholino-, $(C_1-C_9)$heteroarylmorpholino-, $(C_1-C_6)$ alkylmorpholino-, $(C_6-C_{10})$aryl$(C_1-C_6)$ alkylmorpholino-, $(C_1-C_9)$heteroaryl$(C_1-C_6)$ alkylmorpholino-, thiomorpholino-, $(C_1-C_6)$ acylthiomorpholino-, $(C_6-C_{10})$arylthiomorpholino-, $(C_1-C_9)$heteroarylthiomorpholino-, $(C_1-C_6)$ alkylthiomorpholino-, $(C_6-C_{10})$aryl$(C_1-C_6)$ alkylthiomorpholino-, $(C_1-C_9)$heteroaryl$(C_1-C_6)$ alkylthiomorpholino-, piperidino-, $(C_1-C_6)$ acylpiperidino-, $(C_6-C_{10})$arylpiperidino-, $(C_1-C_9)$ heteroarylpiperidino-, $(C_1-C_6)$alkyl piperidino-, $(C_6-C_{10})$aryl$(C_1-C_6)$piperidino-, $(C_1-C_9)$heteroaryl $(C_1-C_6)$alkylpiperidino-, pyrrolidino-, $(C_1-C_6)$ acylpyrrolidino-, $(C_6-C_{10})$arylpyrrolidino-, $(C_1-C_9)$ heteroarylpyrrolidino, $(C_1-C_6)$alkylpyrrolidino-, $(C_6-C_{10})$aryl$(C_1-C_6)$alkylpyrrolidino-, $(C_1-C_9)$ heteroaryl$(C_1-C_6)$alkylpyrrolidino-, $(C_1-C_6)$alkoxy $(C_1-C_6)$acyl-, $(C_1-C_6)$alkylamino$(C_6-C_{10})$aryl-, and $((C_1-C_6)$alkyl$)_2$amino$(C_1-C_6)$acyl-;

(c) $R^7$, or $R^7Y$-, where $R^7$ is selected from the group consisting of piperazino-, $(C_6-C_{10})$arylpiperazino-, $(C_1-C_9)$ heteroarylpiperazino-, $(C_1-C_6)$alkylpiperazino-, $(C_6-C_{10})$ aryl$(C_1-C_6)$alkylpiperazino-, $(C_1-C_9)$heteroaryl$(C_1-C_6)$ alkylpiperazino-, morpholino-, $(C_6-C_{10})$arylmorpholino-, $(C_1-C_9)$heteroarylmorpholino-, $(C_1-C_6)$alkylmorpholino-, $(C_6-C_{10})$aryl$(C_1-C_6)$alkylmorpholino-, $(C_1-C_9)$heteroaryl $(C_1-C_6)$alkylmorpholino-, thiomorpholino-, $(C_6-C_{10})$ arylthiomorpholino-, $(C_1-C_9)$heteroarylthiomorpholino-, $(C_1-C_6)$alkylthiomorpholino-, $(C_6-C_{10})$aryl$(C_1-C_6)$ alkylthiomorpholino-, $(C_1-C_9)$heteroaryl$(C_1-C_6)$ alkylthiomorpholino-, piperidino-, $(C_6-C_{10})$ arylthiopiperidino-, $(C_1-C_9)$heteroarylthiopiperidino-, $(C_1-C_6)$alkylthiopiperidino-, $(C_6-C_{10})$aryl$(C_1-C_6)$ alkylthiopiperidino-, $(C_1-C_9)$heteroaryl$(C_1-C_6)$ alkylthiopiperidino-, pyrolidino-, $(C_6-C_{10})$ arylthiopyrolidino-, $(C_1-C_9)$heteroarylthiopyrolidino-, $(C_1-C_6)$alkylthiopyrolidino-, $(C_6-C_{10})$aryl$(C_1-C_6)$ alkylthiopyrolidino-, $(C_1-C_9)$heteroaryl$(C_1-C_6)$ alkylthiopyrolidino-, and Y, if present, is selected from the group consisting of $(C_1-C_6)$alkyl-, $(C_2-C_6)$alkenyl-, $(C_2-C_6)$alkynyl-, amino, oxygen, thio, sulfinyl, sulfonyl, halo$(C_1-C_6)$alkyl-, and hydroxy$(C_2-C_6)$alkyl-;

(d) $ZR^8$—, where $R^8$ is selected from the group consisting of piperazino-, $(C_6-C_{10})$arylpiperazino-, $(C_1-C_9)$ heteroarylpiperazino-, $(C_1-C_6)$alkylpiperazino-, $(C_6-C_{10})$aryl$(C_1-C_6)$alkylpiperazino-, $(C_1-C_9)$heteroaryl$(C_1-C_6)$alkylpiperazino-, morpholino-, $(C_6-C_{10})$arylmorpholino-, $(C_1-C_9)$heteroarylmorpholino-, $(C_1-C_6)$alkylmorpholino-, $(C_6-C_{10})$aryl$(C_1-C_6)$alkylmorpholino-, $(C_1-C_9)$heteroaryl$(C_1-C_6)$alkylmorpholino-, thiomorpholino-, $(C_6-C_{10})$arylthiomorpholino-, $(C_1-C_9)$heteroarylthiomorpholino-, $(C_1-C_6)$alkylthiomorpholino-, $(C_6-C_{10})$aryl$(C_1-C_6)$alkylthiomorpholino-, $(C_1-C_9)$heteroaryl$(C_1-C_6)$alkylthiomorpholino-, piperidino-, $(C_6-C_{10})$arylthiopiperidino-, $(C_1-C_9)$heteroarylthiopiperidino-, $(C_1-C_6)$alkylthiopiperidino-, $(C_6-C_{10})$aryl$(C_1-C_6)$alkylthiopiperidino-, $(C_1-C_9)$heteroaryl$(C_1-C_6)$alkylthiopiperidino-, pyrolidino-, $(C_6-C_{10})$arylthiopyrolidino-, $(C_1-C_9)$heteroarylthiopyrolidino-, $(C_1-C_6)$alkylthiopyrolidino-, $(C_6-C_{10})$aryl$(C_1-C_6)$alkylthiopyrolidino-, $(C_1-C_9)$heteroaryl$(C_1-C_6)$alkylthiopyrolidino-, and Z is selected from the group consisting of $(C_1-C_6)$alkyl-, $(C_2-C_6)$alkenyl-, $(C_2-C_6)$alkynyl-, amino, oxygen, thio, sulfinyl, sulfonyl, halo$(C_1-C_6)$alkyl-, and hydroxy$(C_2-C_6)$alkyl-;

(e) two or more of $R^2$, when vicinal, together to form one or more further rings of 4, 5, 6 or 7 member atoms selected from the group consisting of phenyl-, naphthyl-, furyl-, thienyl-, thiazolyl-, pyrazolyl-, isothiazolyl-, oxazolyl-, isoxazolyl-, pyrrolyl-, triazolyl-, tetrazolyl-, imidazolyl-, 1,3,5-oxadiazolyl-, 1,2,4-oxadiazolyl-, 1,2,3-oxadiazolyl-, 1,3,5-thiadiazolyl-,-1,2,3-thiadiazolyl-, 1,2,4-thiadiazolyl-, pyridyl-, pyrimidyl-, pyrazinyl-, pyridazinyl-, 1,2,4-triazinyl-, 1,2,3-triazinyl-, 1,3,5-triazinyl-, pyrazolo[3,4-b]pyridinyl-, cinnolinyl-, pteridinyl-, purinyl-, 6,7-dihydro-5H-[1]pyrindinyl-, benzo[b]thiophenyl-, 5,6,7,8-tetrahydroquinolin-3-yl, benzoxazolyl-, benzothiazolyl-, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl-, quinolyl-, phthalazinyl-, quinoxalinyl-, quinazolinyl-, benzoxazinyl-, and wherein said ring(s) are optionally substituted by one or more $(C_1-C_6)$alkyl-, $(C_2-C_6)$alkenyl-, $(C_2-C_6)$alkynyl-, amino-, halo-, hydroxy-, carboxy-, thiol-, nitro-, cyano-, sulfonic-, halo$(C_1-C_6)$alkyl-, and hydroxy$(C_2-C_6)$alkyl-; and (f) two or more of $R^2$ when vicinal, together to form one or more further rings of 3, 4, 5, 6 or 7 member atoms selected from the groups consisting of:

(i) $(C_3-C_{10})$cycloalkyl-, containing zero to two levels of unsaturation, selected from the group consisting of cyclopropyl-, cyclobutyl-, cyclopentyl-, cyclohexyl-, cycloheptyl-, cyclopropenyl-, cyclobutenyl-, cyclopentenyl-, cyclohexenyl-, cycloheptenyl-, 1,3-cyclobutadienyl-, 1,3-cyclopentadienyl-, 1,3-cyclohexadienyl-, 1,4-cyclohexadienyl-, 1,3-cycloheptadienyl-, 1,4-cycloheptadienyl-, bicyclo[3.2.1]octane-, bicyclo[2.2.1]heptane, the norborn-2-ene unsaturated form thereof, and the like, wherein said ring is optionally substituted by hydroxy-, halo-, amino-, trifluoromethyl-, hydroxy$(C_2-C_6)$alkyl-, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$acylamino-, cyano-, nitro-, carboxy-, thiol-, sulfonyl-, $(C_1-C_6)$alkyl-, $(C_2-C_6)$alkenyl-, $(C_2-C_6)$alkynyl-, $(C_1-C_6)$acylamino-, cyano$(C_1-C_6)$alkyl-, trifluoromethyl$(C_1-C_6)$alkyl-, $(C_1-C_3)$alkyl(difluoromethylene)$(C_1-C_3)$alkyl-, halo$(C_1-C_6)$alkyl- or nitro$(C_1-C_6)$alkyl-; and (ii) $(C_3-C_{10})$heterocycloalkyl- selected from the group consisting of pyrrolidinyl-, tetrahydrofuranyl-, dihydrofuranyl-, tetrahydropyranyl-, pyranyl-, thiopyrany-l, aziridinyl-, oxiranyl-, methylenedioxyl-, isoxazolidinyl-,-1,3-oxazolidin-3-yl-, isothiazolidinyl-, 1,3-thiazolidin-3-yl-, 1,2-pyrazolidin-2-yl-, 1,3-pyrazolidin-1-yl-, piperidinyl-, thiomorpholinyl-, 1,2-tetrahydrothiazin-2-yl-, 1,3-tetrahydrothiazin-3-yl-, tetrahydrothiadiazinyl-, morpholinyl-, 1,2-tetrahydrodiazin-2-yl-, 1,3-tetrahydrodiazin-1-yl-, tetrahydroazepinyl-, piperazinyl-, chromenyl-, chromanyl-, where said ring is optionally substituted by hydroxy-, halo-, amino-, trifluoromethyl-, hydroxy$(C_2-C_6)$alkyl-, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$acylamino-, cyano-, nitro-, carboxy-, thiol-, sulfonyl-, $(C_1-C_6)$alkyl-, $(C_2-C_6)$alkenyl-, $(C_2-C_6)$alkynyl-, $(C_1-C_6)$acylamino-, cyano$(C_1-C_6)$alkyl-, trifluoromethyl$(C_1-C_6)$alkyl-, $(C_1-C_3)$alkyl(difluoromethylene)$(C_1-C_3)$alkyl-, halo$(C_1-C_6)$alkyl- or nitro$(C_1-C_6)$alkyl-;

wherein any $(C_1-C_6)$alkyl-, $(C_2-C_6)$alkenyl-, $(C_2-C_6)$alkynyl-, $(C_3-C_{10})$cycloalkyl- or $(C_3-C_{10})$heterocycloalkyl- groups that are, or comprise a portion of, said one to four optional $R^2$ substituents are themselves optionally substituted by deuterium-, hydroxy-, amino-, trifluoromethyl-, cyano-, nitro-, carboxy-, $(C_1-C_4)$alkoxy-, $(C_1-C_6)$acyloxy-, $(C_1-C_6)$alkylamino-, $((C_1-C_6)$alkyl$)_2$amino-, $(C_1-C_6)$alkyl-$(C_2-C_6)$alkenyl-, $(C_2-C_6)$alkynyl-, $(C_1-C_6)$acylamino-, $(C_3-C_{10})$cycloalkyl-, $(C_3-C_{10})$heterocycloalkyl-, cyano$(C_1-C_6)$alkyl-, trifluoromethyl$(C_1-C_6)$alkyl-, nitro$(C_1-C_6)$alkyl-, and $(C_1-C_6)$acylamino-; and.

$R^3$ represents one or more optional substituents on a ring carbon atom, including at X where X is —$CH_2$—, selected from the groups consisting of $(C_1-C_6)$alkyl-, trihalo$(C_1-C_6)$alkyl- that is preferably trifluoromethyl-, deuterium, and fluorine.

According to the practice of the invention, with respect to the structural component of compounds of formula I that is represented by

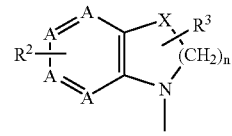

preferred examples include those where the ring structure is contributed by 1,2,3,4-tetrahydroquinoline; 1,2,3,4-tetrahydroquinoxaline; 3,4-dihydro-1H-quinoxaline-2-one (also named 2-oxo-1,2,3,4-tetrahydroquinoxaline); 3,4-dihydro-2H-benzo[1,4]oxazine; 2,3-dihydro-1H-indole; and 3,4-dihydro-2H-benzo[1,4]thiazine, respectively, as depicted below.

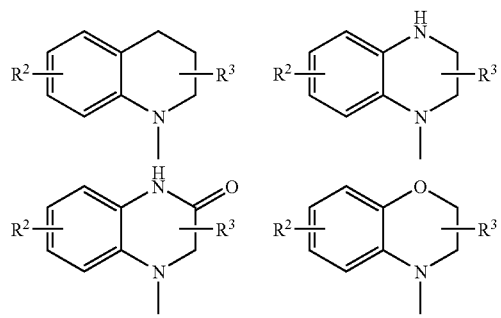

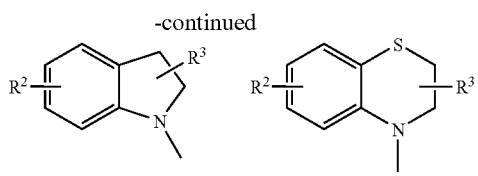

Preferred examples of the above six structures include 6-methoxy-1,2,3,4-tetrahydroquinoline; 4-methyl-1,2,3,4-tetrahydroquinoline; 7-(trifluoromethyl)-1,2,3,4-tetrahydroquinoline; 8-methyl-1,2,3,4-tetrahydroquinoline, 6-hydroxy-1,2,3,4-tetrahydroquinoline; 8-chloro-1,2,3,4-tetrahydroquinoline, 7-chloro-1,2,3,4-tetrahydroquinoline; 6-benzyloxy-7-methoxy-1,2,3,4-tetrahydroquinoline; 6,7-dimethyl-1,2,3,4-tetrahydroquinoxaline; 1,2,3,4-tetrahydroquinoxaline; 1-phenylsulfonyl-1,2,3,4-tetrahydroquinoxaline; 6-Methyl-1,2,3,4-tetrahydroquinoline; 3,4-dihydro-2H-benzo[1,4]oxazine; 5-Fluoro-2,3-dihydro-1H-indole; 1,2,3,4-tetrahydroquinoxaline; and 3,3-dimethyl-2,3-dihydro-1H-indole.

In additional embodiments of the invention, the

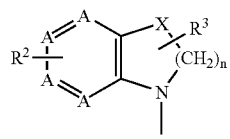

structure is defined, for example, by
2,3-Dihydro-1H-pyrrolo[2,3-b]pyridine; 2,3-Dihydro-1H-pyrrolo[2,3-c]pyridine; 2,3-Dihydro-1H-pyrrolo[3,2-c]pyridine; 2,3-Dihydro-1H-pyrrolo[3,2-b]pyridine; 6,7-Dihydro-5H-pyrrolo[3,2-d]pyrimidine; 6,7-Dihydro-5H-pyrrolo[3,2-d][1,2,3]triazine; 6,7-Dihydro-5H-pyrrolo[2,3-d][1,2,3]triazine; 1,4,5,7-Tetraaza-indan; 1,4,6,7-Tetraaza-indan; 6,7-Dihydro-5H-pyrrolo[2,3-c]pyridazine; 2,3-Dihydro-1H-pyrrolo[2,3-d]pyridazine; 6,7-Dihydro-5H-pyrrolo[3,2-c]pyridazine; 6,7-Dihydro-5H-pyrrolo[2,3-b]pyrazine; 6,7-Dihydro-5H-pyrimido[4,5-b][1,4]oxazine; 5,6,7,8-Tetrahydro-pteridine; 1,2,3,4-Tetrahydro-pyrido[2,3-b]pyrazine; 1,2,3,4-Tetrahydro-pyrido[3,4-b]pyrazine; 1,2,3,4-Tetrahydro-pyrido[3,4-b]pyrazine; 1,2,3,4-Tetrahydro-pyrido[2,3-b]pyrazine; 5,6,7,8-Tetrahydro-pyrazino[2,3-c]pyridazine; 5,6,7,8-Tetrahydro-pteridine; 1,2,3,4-Tetrahydro-pyrazino[2,3-d]pyridazine; 5,6,7,8-Tetrahydro-pyrazino[2,3-c]pyridazine; 1,2,3,4-Tetrahydro-pyrazino[2,3-b]pyrazine; 5,6,7,8-Tetrahydro-pyrazino[2,3-e][1,2,4]triazine; 5,6,7,8-Tetrahydro-pyrazino[2,3-e][1,2,4]triazine; 5,6,7,8-Tetrahydro-pyrazino[2,3-d][1,2,3]triazine; 5,6,7,8-Tetrahydro-pyrazino[2,3-d][1,2,3]triazine; 2,3-Dihydro-1H-4-oxa-1,5-diaza-naphthalene; 2,3-Dihydro-1H-4-oxa-1,6-diaza-naphthalene; 3,4-Dihydro-2H-1-oxa-4,6-diaza-naphthalene; 3,4-Dihydro-2H-1-oxa-4,5-diaza-naphthalene; 7,8-Dihydro-6H-5-oxa-1,2,8-triaza-naphthalene; 3,4-Dihydro-2H-1-oxa-4,6,7-triaza-naphthalene; 6,7-Dihydro-5H-8-oxa-1,2,5-triaza-naphthalene; 3,4-Dihydro-2H-1-oxa-4,5,8-triaza-naphthalene; 7,8-Dihydro-6H-pyrimido[5,4-b][1,4]oxazine; 6,7-Dihydro-5H-pyrimido[4,5-b][1,4]oxazine; 6,7-Dihydro-5H-8-oxa-1,2,3,5-tetraaza-naphthalene; 6,7-Dihydro-5H-8-oxa-1,2,4,5-tetraaza-naphthalene; 7,8-Dihydro-6H-5-oxa-1,2,3,8-tetraaza-naphthalene; 6,7-Dihydro-5H-8-oxa-1,2,4,5-tetraaza-naphthalene; 2,3-Dihydro-1H-pyrido[3,2-b][1,4]thiazine; 2,3-Dihydro-1H-4-thia-1,6-diaza-naphthalene; 3,4-Dihydro-2H-1-thia-4,6-diaza-naphthalene; 3,4-Dihydro-2H-pyrido[3,2-b][1,4]thiazine; 7,8-Dihydro-6H-5-thia-1,2,8-triaza-naphthale; 3,4-Dihydro-2H-1-thia-4,6,7-triaza-naphthalene; 6,7-Dihydro-5H-8-thia-1,2,5-triaza-naphthalene; 6,7-Dihydro-5H-pyrimido[4,5-b][1,4]thiazine; 7,8-Dihydro-6H-pyrimido[5,4-b][1,4]thiazine; 3,4-Dihydro-2H-1-thia-4,5,8-triaza-naphthalene; 6,7-Dihydro-5H-8-thia-1,2,4,5-tetraaza-naphthalene; 7,8-Dihydro-6H-5-thia-1,2,4,8-tetraaza-naphthalene; 7,8-Dihydro-6H-5-thia-1,2,3,8-tetraaza-naphthalene; 6,7-Dihydro-5H-8-thia-1,2,3,5-tetraaza-naphthalene; 5,6,7,8-Tetrahydro-pyrido[3,2-d]pyrimidine; 1,2,3,4-Tetrahydro-pyrido[2,3-d]pyridazine; 5,6,7,8-Tetrahydro-pyrido[2,3-b]pyrazine; 5,6,7,8-Tetrahydro-pyrido[3,2-e][1,2,4]triazine; 5,6,7,8-Tetrahydro-pyrido[2,3-e][1,2,4]triazine; 5,6,7,8-Tetrahydro-pyrido[3,2-d][1,2,3]triazine; and 5,6,7,8-Tetrahydro-pyrido[2,3-d][1,2,3]triazine.

It is additionally preferred that one or more of substituents $R^2$ be selected from the groups consisting of:

(a) $(C_1-C_6)$alkyl-, $(C_1-C_6)$alkynl-, $(C_1-C_6)$alkoxy-, trihalo$(C_1-C_6)$alkyl- that is preferably trifluoromethyl-, $(C_1-C_6)$alkylamino-, $((C_1-C_6)_2)$dialkylamino-, amino-, cyano, and halo-; and (b) benzyloxy-, phenylsulfonyl-, phenylaminocarbonyl-, $(C_1-C_9)$heteroarylsulfonyl-, and $(C_1-C_9)$heteroarylaminocarbonyl-, optionally substituted by one or more groups selected from the group consisting of $(C_1-C_6)$alkyl-, $(C_2-C_6)$alkynyl-, trihalo$(C_1-C_6)$alkyl—that is preferably trifluoromethyl-, $(C_1-C_6)$alkoxy-, $(C_1-C_6)$alkylamino-, $((C_1-C_6)_2)$alkylamino-, and halo.

According to the practice of the invention, preferred examples of $R^1$ include $(C_6-C_{10})$aryl-, and $(C_1-C_9)$heteroaryl—wherein said $R^1$ group is optionally substituted by one or more groups, each independently selected from hydroxy, halo, amino, $(C_1-C_6)$alkyl-, $(C_1-C_6)$alkoxy-, trihalo$(C_1-C_6)$alkyl—that is preferably trifluoromethyl-, $(C_1-C_6)$alkynl-, $(C_1-C_6)$alkylamino-, $((C_1-C_6)_2)$dialkylamino-, carboxy-, $(C_1-C_6)$alkoxycarbonyl-, $(C_1-C_6)$acyloxy-,and $(C_1-C_6)$acylamino-.

In a preferred embodiment of the invention, $R^1$ is a $(C_1-C_9)$heteroaryl- group selected from the group consisting of pyridyl-, indazolyl-, indolyl-, 1,3-dihydro-benzoimidazol-2-one, thienyl-, oxazoyl-, 2H-pyrazolyl-, 1H-pyrazolyl-, isooxazoyl-, thiazolyl(fix,name), and isothiazoyl-, and is optionally substituted by one or more groups, each independently selected from hydroxy-, halo-, amino-, $(C_1-C_6)$alkyl-, $(C_1-C_6)$alkoxy-, trihalo$(C_1-C_6)$alkyl- that is preferably trifluoromethyl-, $(C_1-C_6)$alkynl-, $(C_1-C_6)$alkylamino-, $((C_1-C_6)_2)$dialkylamino-, carboxy-, $(C_1-C_6)$alkoxycarbonyl-, $(C_1-C_6)$acyloxy-, and $(C_1-C_6)$acylamino-.

In an additionally preferred embodiment of the invention, $R^1$ is phenyl, optionally substituted with one to five substituents, that are each independently selected from hydroxy-, halo-, amino-, $(C_1-C_6)$alkyl-, $(C_1-C_6)$alkoxy-, trihalo$(C_1-C_6)$alkyl- that is preferably trifluoromethyl-, $(C_1-C_6)$alkynl-, $(C_1-C_6)$alkylamino-, $((C_1-C_6)_2)$dialkylamino-, carboxy, $(C_1-C_6)$alkoxycarbonyl-, $(C_1-C_6)$acyloxy-, and $(C_1-C_6)$acylamino-.

Particularly preferred examples of $R^1$ include 3,4,5-trimethoxyphenyl-; 2,3-dimethyl-1H-indol-5-yl; 3,4-dihydro-2H-quinolin-1-yl; and 6-morpholin-4-yl-pyridin-3-yl.

Representative compounds of the invention include:

(a) 1-[(2-anilino)-4-pyrimidinyl]-6-methyl-1,2,3,4-tetrahydroquinoline;

(b) 1-[2-[(4-bromophenyl)amino]-4-pyrimidinyl]-6-methyl-1,2,3,4-tetrahydroquinoline;

(c) 1-[2-[(4-methoxyphenyl)amino]-4-pyrimidinyl]-6-methyl-1,2,3,4-tetrahydroquinoline;
(d) 1-[2-[(1H-indazole-5-yl)]-4-pyrimidyl]-6-methyl-1,2,3,4-tetrahydroquinoline;
(e) 1-[2-[(4-phenoxyphenyl)amino]-4-pyrimidinyl]-6-methyl-1,2,3,4-tetrahydroquinoline;
(f) 1-[2-[(3,4-dimethoxyphenyl)amino]-4-pyrimidinyl]-6-methyl-1,2,3,4-tetrahydroquinoline;
(g) 1-[2-[(3,4,5-trimethoxyphenyl)amino]-4-pyrimidinyl]-6-methyl-1,2,3,4-tetrahydroquinoline;
(h) 1-[2-[(4,N-phenylaminophenyl)amino]-4-pyrimidinyl]-6-methyl-1,2,3,4-tetrahydroquinoline;
(i) [4-(6-Methyl-3,4-dihydro-2H-quinolin-1-yl)-pyrimidin-2-yl]-(6-morpholin-4-yl-pyridin-3-yl)-amine;
(j) 5-[4-(6-Methyl-3,4-dihydro-2H-quinolin-1-yl)-pyrimidin-2-ylamino]-1,3-dihydro-benzoimidazol-2-one;
(k) (2,3-Dimethyl-1H-indol-5-yl)-[4-(6-methyl-3,4-dihydro-2H-quinolin-1-yl)-pyrimidin-2-yl]-amine;
(l) [4-(6-Methyl-3,4-dihydro-2H-quinolin-1-yl)-pyrimidin-2-yl]-(2-methyl-2H-pyrazol-3-yl)-amine;
(m) (6-Methoxy-pyridin-3-yl)-[4-(6-methyl-3,4-dihydro-2H-quinolin-1-yl)-pyrimidin-2-yl]-amine;
(n) (4-Fluoro-3-methyl-phenyl)-[4-(6-methyl-3,4-dihydro-2H-quinolin-1-yl)-pyrimidin-2-yl]-amine;
(o) (5-Cyclopropyl-2H-pyrazol-3-yl)-[4-(6-methyl-3,4-dihydro-2H-quinolin-1-yl)-pyrimidin-2-yl]-amine;
(p) 4-Benzyl-N3-[4-(6-methyl-3,4-dihydro-2H-quinolin-1-yl)-pyrimidin-2-yl]-1H-pyrazole-3,5-diamine;
(q) [4-(6-Methyl-3,4-dihydro-2H-quinolin-1-yl)-pyrimidin-2-yl]-(4-methyl-thiazol-2-yl)-amine; and
(r) [4-(6-Methyl-3,4-dihydro-2H-quinolin-1-yl)-pyrimidin-2-yl]-(5-methyl-1H-pyrazol-3-yl)-amine.

Additional preferred compounds of the invention include [4-(3,4-Dihydro-2H-quinolin-1-yl)-pyrimidin-2-yl]-(6-pyrrolidin-1-yl-pyridin-3-yl)-amine; (1-Cyclopentyl-1H-indol-6-yl)-[4-(6-methyl-3,4-dihydro-2H-quinolin-1-yl)-pyrimidin-2-yl]-amine; [4-(6-Methyl-3,4-dihydro-2H-quinolin-1-yl)-pyrimidin-2-yl]-oxazol-4-yl-amine; (3,4-Dichloro-phenyl)-[4-(6-methyl-3,4-dihydro-2H-quinolin-1-yl)-pyrimidin-2-yl]-amine; and [4-(3,4-Dihydro-2H-quinolin-1-yl)-pyrimidin-2-yl]-isothiazol-3-yl-amine.

Additional preferred compounds of the invention include:
2-({5-[4-(2,3-Dihydro-benzo[1,4]oxazin-4-yl)-pyrimidin-2-ylamino]-pyridin-2-yl}-methyl-amino)-ethanol;
N-{5-[4-(3-Oxo-3,4-dihydro-2H-quinoxalin-1-yl)-pyrimidin-2-ylamino]-pyridin-2-yl}-acetamide;
3-Chloro-N-[4-(4-methyl-3-oxo-3,4-dihydro-2H-quinoxalin-1-yl)-pyrimidin-2-yl]-benzamide;
[4-(2,3-Dihydro-benzo[1,4]thiazin-4-yl)-pyrimidin-2-yl]-oxazol-4-yl-amine;
N-[4-(5-Fluoro-2,3-dihydro-indol-1-yl)-pyrimidin-2-yl]-3-methoxy-benzenesulfonamide;
[4-(5,6-Dihydro-pyrrolo[2,3-d]pyrimidin-7-yl)-pyrimidin-2-yl]-(2-trifluoromethyl-phenyl)-amine;
6-Methoxy-1-[2-(pyridazin-3-ylamino)-pyrimidin-4-yl]-2,3-dihydro-1H-quinolin-4-one;
2-{5-[4-(3,4-Dihydro-2H-quinoxalin-1-yl)-pyrimidin-2-ylamino]-indol-1-yl}-ethanol;
(2H-Pyrazol-3-yl)-[4-(7-trifluoromethyl-3,4-dihydro-2H-quinolin-1-yl)-pyrimidin-2-yl]-amine;
1-[4-(3,4-Dihydro-2H-[1,5]naphthyridin-1-yl)-pyrimidin-2-yl]-3-ethyl-urea;
1-[4-(2,3-Dihydro-benzo[1,4]oxazin-4-yl)-pyrimidin-2-yl]-3-(2-ethoxy-ethyl)-urea;
[4-(3,3-Dimethyl-2,3-dihydro-indol-1-yl)-pyrimidin-2-yl]-carbamic acid tert-butyl ester;
3-Cyano-N-[4-(7-methoxy-2,3,4,5-tetrahydro-benzo[b]azepin-1-yl)-pyrimidin-2-yl]-benzamide;
Isoxazol-4-yl-[4-(2,3,4,5-tetrahydro-benzo[b][1,4]diazepin-1-yl)-pyrimidin-2-yl]-amine;
(3,4-Dichloro-phenyl)-[4-(3,4-dihydro-2H-benzo[b][1,4]thiazepin-5-yl)-pyrimidin-2-yl]-amine;
(6-Aziridin-1-yl-pyridin-3-yl)-[4-(5-methanesulfonyl-2,3-dihydro-indol-1-yl)-pyrimidin-2-yl]-amine;
$N^2$-Cyclopropyl-$N^5$-[4-(6-fluoro-3,4-dihydro-2H-quinolin-1-yl)-pyrimidin-2-yl]-pyridine-2,5-diamine; and
Benzo[1,3]dioxole-5-carboxylic acid [4-(6-fluoro-3,4-dihydro-2H-quinolin-1-yl)-pyrimidin-2-yl]-amide.

The compounds and pharmaceutical compositions of this invention include all conformational isomers of compounds of formula I (e.g., cis and trans isomers, whether or not involving double bonds). The compounds of the invention include all optical isomers of the compounds of formula I (e.g., enantiomers and diastereomers), as well as racemic, diastereomeric and other mixtures of all such isomers. This invention further relates to tautomers and stereoisomers of the compounds of formula (I), and mixtures of any of the aforementioned forms.

The present invention also relates to the pharmaceutically acceptable acid addition salts of compounds of the formula (I). The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The present invention also relates to the pharmaceutically acceptable base addition salts of compounds of the formula (I). The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The subject invention also includes isotopically-labelled compounds, which are identical to those recited in Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^3$H, can afford certain therapeutic advantages resulting from greater metabolic stability, for example increased in vivo half-life or reduced dosage requirements and, hence, may be preferred in some circumstances. Isotopically labelled compounds of Formula (I) of this invention and prodrugs thereof can generally be prepared by carrying out the procedures disclosed in the Schemes and/or in the Examples and Preparations below, by substituting a readily available isotopically labelled reagent for a non-isotopically labelled reagent.

In the practice of the invention, preferably the mammalian patient is a human, but the invention is broadly applicable to the treatment of other mammals, such as farm animals and companion animals.

The present invention relates to a pharmaceutical composition for treatment or prevention of conditions in a mammalian patient, where therapeutic benefit is achieved by downregulating T-cell mediated immune response, comprising an effective amount of a compound according to formula I, and a pharmaceutical carrier.

The present invention relates to a pharmaceutical composition for the treatment or prevention of transplant rejection in a mammal, comprising an effective amount of a compound according to formula I, and a pharmaceutical carrier.

The present invention relates to a pharmaceutical composition for treatment or prevention of autoimmune disease in a mammal, comprising an effective amount of a compound according to formula I, and a pharmaceutical carrier.

The present invention also relates to a pharmaceutical composition for treating inflammatory disease in a mammal, comprising an effective amount of a compound according to formula I, and a pharmaceutical carrier.

The present invention also relates to a pharmaceutical composition for treating allergy in a mammal, comprising an effective amount of a compound according to formula 1, and a pharmaceutical carrier.

The present invention also relates to a pharmaceutical composition for treating T-cell leukemias and T-cell lymphomas in a mammal, comprising an effective amount of a compound according to formula I, and a pharmaceutical carrier.

The present invention also relates to a pharmaceutical composition for the treatment of diseases in a mammal, wherein treatment can be effected by inhibiting activation of T-cells, or the results of said activation, comprising an effective amount of a compound according to formula I, and a pharmaceutical carrier.

The present invention relates to a method for treating or preventing transplant rejection in a mammal.

The present invention further relates to a method for treating or preventing autoimmune disease in a mammal.

The present invention further relates to a method for treating or preventing allergic disease in a mammal.

The present invention further relates to a method for treating or preventing inflammatory disease in a mammal.

The present invention also relates to inhibiting T-cell mediated immune response in a mammalian patient, wherein this is beneficial to the mammal nothwithstanding that said immune function was within the normal range.

In the practice of said methods, there is administered a pharmaceutical composition of the invention comprising a compound according to formula I, and a pharmaceutical carrier.

An additional embodiment of the invention includes a compound of formula (I), or a pharmaceutically acceptable salt, solvate, or hydrate of any such compound, for administration in pharmaceutically acceptable form, in combination with one or more additional agents which have an anti-inflammatory effect, or which themselves can modulate one or more components or processes of the mammalian immune system.

Definitions

In connection with the practice of the invention, the following definitions will generally apply.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "transplant" refers to transplanted cells, tissues, and organs or portions of organs. The term "transplant" also refers to macromolecules that are normally associated with the transplanted cells, tissues, and organs, whether intracellular, membrane associated, or extracellular in nature. In this regard, a category of macromolecules that is of particular interest refers to those associated with the extracellular matrix of a transplanted tissue. T-cell mediated immune response against such macromolecules can cause failure of the transplant as a whole. "Transplant" includes both allografts and xenografts.

The term "alkyl", as used herein, unless otherwise indicated, includes saturated monovalent hydrocarbon radicals having straight, branched or cyclic moieties or combinations thereof. Similarly, the terms "alkenyl" and "alkynl" define hydrocarbon radicals having straight, branched or cyclic moities wherein at least one double bond, or at least one triple bond, respectively, is present. Such definitions also apply when the alkyl, alkenyl or alkynyl group is present within another group, such as alkoxy or alkylamine.

The term "alkoxy", as used herein, includes O-alkyl groups wherein "alkyl" is as defined above.

The term "halo", as used herein, unless otherwise indicated, includes fluoro, chloro, bromo or iodo.

An "aryl" group as used herein, unless otherwise indicated, includes an organic radical derived from a monocyclic or bicyclic ($C_6$–$C_{10}$) aromatic hydrocarbon compound by removal of a hydrogen radical from a ring carbon of the aryl compound. An aryl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative aryl groups are phenyl and naphthyl.

A "heteroaryl" group as used herein, unless otherwise indicated, includes an organic radical derived from a monocyclic or bicyclic ($C_1$–$C_9$) aromatic heterocyclic compound by removal of a hydrogen radical from a ring atom of the heteroaryl compound, said ring atom being uncharged in said compound. A heteroaryl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative heteroaryl- groups include furyl-, thienyl-, thiazolyl-, pyrazolyl-, isothiazolyl-, oxazolyl-, isoxazolyl-, pyrrolyl-, triazolyl-, tetrazolyl-, imidazolyl-, 1,3,5-oxadiazolyl-, 1,2,4-oxadiazolyl-, 1,2,3-oxadiazolyl-, 1,3,5-thiadiazolyl-, 1,2,3-thiadiazolyl-, 1,2,4-thiadiazolyl-, pyridyl-, pyrimidyl-, pyrazinyl-, pyridazinyl-, 1,2,4-triazinyl-, 1,2,3-triazinyl-, 1,3,5-triazinyl-, pyrazolo[3,4-b]pyridinyl-, cinnolinyl-, pteridinyl-, purinyl-, 6,7-dihydro-5H-[1]pyrindinyl-, benzo[b]thiophenyl-, 5,6,7,8-tetrahydro-quinolin-3-yl-, benzoxazolyl-, benzothiazolyl-, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl-, quinolyl-, phthalazinyl-, quinoxalinyl-, quinazolinyl-, and benzoxazinyl-; and the like.

A "cycloalkyl" group as used herein, unless otherwise indicated, includes an organic radical derived from a monocyclic $(C_3-C_{10})$cycloalkyl- compound, by removal of a hydrogen radical from a ring carbon of the cycloalkyl-compound. A cycloalkyl- group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative cycloalkyl- groups include cyclopropyl-, cyclobutyl-, cyclopentyl-, cyclohexyl-, cycloheptyl-, cyclopropenyl-, cyclobutenyl-, cyclopentenyl-, cyclohexenyl-, cycloheptenyl-, 1,3-cyclobutadienyl-, 1,3-cyclopentadienyl-, 1,3-cyclohexadienyl-, 1,4-cyclohexadienyl-, 1,3-cycloheptadienyl-, 1,4-cycloheptadienyl-, bicyclo[3.2.1]octane-, bicyclo-[2.2.1]heptane-, and the norborn-2-ene unsaturated form thereof. Thus, the term cycloalkyl- also includes cycloalkenyl- groups having one or two double bonds.

A "heterocycloalkyl" group as used herein, unless otherwise indicated, includes an organic radical derived from a monocyclic $(C_3-C_{10})$heterocycloalkyl compound by removal of a hydrogen radical from a ring atom of the heterocycloalkyl compound. A heterocycloalkyl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative heterocycloalkyl- groups include pyrrolidinyl-, tetrahydrofuranyl-, dihydrofuranyl-, tetrahydropyranyl-, pyranyl-, thiopyranyl-, aziridinyl-, oxiranyl-, methylenedioxyl-, chromenyl-, isoxazolidinyl-, 1,3-oxazolidin-3-yl-, isothiazolidinyl-, 1,3-thiazolidin-3-yl-, 1,2-pyrazolidin-2-yl-, 1,3-pyrazolidin-1-yl-, piperidinyl-, thiomorpholinyl-, 1,2-tetrahydrothiazin-2-yl-, 1,3-tetrahydrothiazin-3-yl-, tetrahydrothiadiazinyl-, morpholinyl-, 1,2-tetrahydrodiazin-2-yl-, 1,3-tetrahydrodiazin-1-yl-, tetrahydroazepinyl-, piperazinyl-, and chromanyl-.

In connection with the terms "aryl" group, "heteroaryl" group, "cycloalkyl" group and "heterocycloalkyl" group, as herein defined, the term "optionally substituted" means that one or more chemically and pharmaceutically acceptable functional groups may be bonded thereto. Such a group contributes properties useful to production, storage, or use of the inventive compounds as pharmaceuticals, or at least does not substantially negate their pharmacological activity. Such suitable substituents may be determined by those skilled in the art. Illustrative examples of suitable substituents include, but are not limited to, hydroxy, halo, amino, trifluoromethyl, carboxy, $(C_1-C_6)$alkoxy-, $(C_1-C_6)$acyloxy-, $(C_1-C_6)$alkylamino-, $((C_1-C_6)$alkyl$)_2$amino-, $(C_1-C_6)$acylamino-, cyano, nitro, $(C_1-C_6)$alkyl-, $(C_2-C_6)$alkenyl-, $C_2-C_6)$alkynyl-, $(C_1-C_6)$acylamino-, cyano$(C_1-C_6)$alkyl-, trifluoromethyl$(C_1-C_6)$alkyl-, nitro$(C_1-C_6)$alkyl-, $(C_1-C_3)$alkyl(difluoromethylene)$(C_1-C_3)$alkyl-, $(C_1-C_6)$acylamino $(C_1-C_6)$alkyl-, $(C_1-C_6)$alkoxy$(C_1-C_6)$acylamino-, amino $(C_1-C_6)$acyl-, amino$(C_1-C_6)$acyl$(C_1-C_6)$alkyl-, $(C_1-C_6)$alkylamino$(C_1-C_6)$acyl-, $((C_1-C_6)$alkyl$)_2$amino$(C_1-C_6)$acyl-, $(C_3-C_{10})$cycloalkyl$(C_1-C_6)$alkyl-, $(C_1-C_6)$acyloxy $(C_1-C_6)$alkyl-, $(C_2-C_6)$alkoxy$(C_1-C_6)$alkyl-, piperazinyl $(C_1-C_6)$alkyl-, $(C_1-C_6)$acylamino$(C_1-C_6)$alkyl-, $(C_6-C_{10})$aryl$(C_1-C_6)$alkoxy$(C_1-C_6)$alkyl-, $(C_2-C_9)$heteroaryl $(C_1-C_6)$alkoxy$(C_1-C_6)$alkyl-, $(C_1-C_6)$alkylthio$(C_1-C_6)$alkyl-, $(C_6-C_{10})$arylthio$(C_1-C_6)$alkyl-, $(C_1-C_6)$alkylsulfinyl $(C_1-C_6)$alkyl-$(C_6-C_{10})$arylsulfinyl$(C_1-C_6)$alkyl-, $(C_1-C_6)$alkylsulfonyl$(C_1-C_6)$alkyl-, $(C_6-C_{10})$arylsulfonyl$(C_1-C_6)$alkyl-, amino$(C_1-C_6)$alkyl-, $(C_1-C_6)$alkylamino$(C_1-C_6)$alkyl-, $(C_1-C_6)$alkyl(difluoromethylene)-, $(C_1-C_3)$alkyl (difluoromethylene)$(C_1-C_3)$alkyl-, $(C_1-C_6)$alkoxy$(C_1-C_6)$acyl-, $(C_1-C_6)$alkylamino$(C_1-C_6)$acyl-, $((C_1-C_6)$alkyl$)_2$amino$(C_1-C_6)$acyl-, $(C_6-C_{10})$aryl-, $(C_5-C_9)$heteroaryl-, $(C_6-C_{10})$aryl$(C_1-C_6)$alkyl-, $(C_2-C_9)$heteroaryl$(C_1-C_6)$alkyl-, $(C_6-C_{10})$aryl$(C_6-C_{10})$aryl-, $(C_6-C_{10})$aryl$(C_6-C_{10})$aryl$(C_1-C_6)$alkyl-$(C_3-C_{10})$cycloalkyl-, $(C_3-C_6)$cycloalkyl $(C_1-C_6)$alkyl-, $(C_3-C_{10})$heterocycloalkyl-, $(C_3-C_{10})$heterocycloalkyl$(C_1-C_6)$alkyl-, hydroxy$(C_2-C_6)$alkyl-, $(C_1-C_6)$acyloxy$(C_2-C_6)$alkyl-, $(C_1-C_6)$alkoxy$(C_2-C_6)$alkyl-, piperazinyl$(C_1-C_6)$alkyl-, $(C_1-C_6)$acylamino $(C_1-C_6)$alkyl-, $(C_6-C_{10})$aryl$(C_1-C_6)$alkoxy$(C_1-C_6)$alkyl-, $(C_2-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio$(C_1-C_6)$alkyl-, $(C_1-C_6)$alkylsulfinyl$(C_1-C_6)$alkyl-, $(C_6-C_{10})$arylsulfinyl $(C_1-C_6)$alkyl-, $(C_1-C_6)$alkylsulfonyl$(C_1-C_6)$alkyl-, $(C_6-C_{10})$arylsulfonyl$(C_1-C_6)$alkyl-, amino$(C_1-C_6)$alkyl-, $(C_1-C_6)$alkylamino$(C_1-C_6)$alkyl-, and $((C_1-C_6)$alkyl$)_2$amino$(C_1-C_6)$alkyl.

The present invention, and additional embodiments thereof, are further described in the detailed description of the invention which follows directly.

DETAILED DESCRIPTION OF THE INVENTION

Practice of the Invention

Characterized in its broadest sense, the present invention is directed to recognizing conditions where therapeutic benefit can be achieved by downregulating T-cell mediated immune response. Depending on the involved clinical condition, the immune response that is downregulated may be normal or abnormal, or otherwise beneficial. In a preferred embodiment of the invention, therapeutic modulation of T-cell mediated processes is achieved in a mammalian patient through the administration of compounds that interefere with, or otherwise modify, T-cell activation, and/or other T-cell functions that result from such activation. Generally speaking, such events binding of an antigen (including a self-antigen) to a T-cell.

T-cell mediated immune responses are involved, for example, in delayed-type hypersensitivity, lysis of tumor cells or cells that express viral antigens, resistance to intracellular pathogens, allergic contact dermatitis, rejection of allografts and xenografts, graft versus host reactions, certain autoimmune diseases, and various types of allergy. Preventing activation of T-cells thus represents an important point of intervention for cell mediated immune responses when this is therapeutically appropriate.

For purposes of description, clinical conditions that can be treated according to the practice of the present invention may be divided into three principal categories:

(1) prevention of transplant rejection, where cells, tissues, or organs (or parts thereof) have been transplanted into a patient, and the normal and otherwise proper immune response against the transpant must be prevented;

(2) treatment of various disease states where "normal" immune system action leads, directly or indirectly, to clinical manifestations that are not desired, for example is circumstances involving damaging inflammation, and allergy; and (3) various disease states, characterized in whole or part as autoimmune diseases, wherein an immune response is mounted against the body's own tissues.

The present invention is practiced with respect to all of the diseases, clinical conditions, and the like, that are discussed below.

Of course, given the complex nature of many disease states or clinical conditions, more than one of the above categories may be relevant in particular circumstances. It must be emphasized that these categories are arbitrary and merely descriptive. For example, with respect to insulin dependent (juvenile/type I) diabetes (see below), treatment at onset is best characterized as prevention of autoimmune disease, whereas immune suppression in the mature disease may be for the purpose of protecting transplanted pancreatic beta cells.

An additional category relates to suppression of an immune response against a therapeutic macromolecule that is administered to (or expressed in) a patient, wherein said macromolecule is otherwise foreign to the patient. Examples include proteins expressed from gene therapy and covalently modified proteins, such as PEGylated proteins. It should be noted that, on occasion, immune response can also occur even against a protein that has an amino acid sequence identical to that encoded by a patient's own genome. Under these circumstances, the protein may have been expressed in the body at levels, or in places, that are atypical, or in an atypical combination with other macromolecules, or the immune response may occur for unknown reasons.

In elaboration of these demonstrative categories, examples of circumstances where it is appropriate to prevent activation of T-cells, and/or to down regulate T-cell mediated immune response, are as follows.

(1) Organ, tissue, and cell transplants between individuals of the same species (allograft transplantations) are an important medical procedure for which there is often no substitute, since the complicated functions of the kidney, heart, bone marrow, lung, or liver, for example, cannot be duplicated. Unfortunately, transplants between individuals very often end in rejection of the transplant. For example, if an allograft of donor skin is positioned on an excised area of a recipient patient, the graft will at first successfully vascularize and proliferate. However, after a brief period of time (perhaps 7–10 days), the site typically becomes subject to severe inflammation, and the transplanted skin withers and is sloughed. A repeat transplant from the same donor is subject to more rapid rejection. It is well known that such events are mediated by transplantation antigens including the major histocompatibility complex of glycoproteins (MHC, also termed HLA in humans) which are expressed from perhaps 20 genes. The HLA protein products, when expressed on cell surfaces, play a major role in presenting peptide fragments of antigen to T-cells at their antigen-specific receptors, the TcR. The HLA glycoproteins vary tremendously from individual to individual, and when recognized by receptive T-cells, are responsible for the typically complete rejection of the donor tissue. Interfering with activation of the T-cells, will permit a wider variety of transplant procedures to be successfully performed.

Xenograft transplants are also subject to rejection. Important examples of such transplants include primate-to-human and pig-to-human, and involve numerous organs and tissues including, without limitation, heart and heart valve, kidney, skin, pancreas, and the like.

(2) It is well known that antigens can elicit inflammatory responses having an intensity that does not necessary correlate with the level of circulating antibodies. Delayed-type hypersensitivity (DTH) reactions are an example of such responses, in which activated T-cells participate.

In a general sense, inflammation is a protective response to local injury or other abnormal condition, and involves blood vessels, cells that circulate in the blood vessels, and nearby connective tissue. The early phase of an inflammatory response typically begins with hyperemia, edema, and margination of circulating white blood cells. The white blood cells (including phagocytic leukocytes, and lymphocytes) then penetrate between the endothelial cells of the blood vessel wall, and enter the tissue. The leakage of water and protein into the damaged area (edema) also permits entry of antibodies, facilitates washing away of toxic substances and debris, and permits direct contact of defending white cells, including phagocytic cells, with infecting agents. Local inflammatory responses are also associated with systemic changes including fever, and an increase in the number of circulating leukocytes.

A large number of additional cellular components participate in the inflammatory response. In this regard, the complement system should be mentioned. Complement consists of about 25–30 proteins, some of which circulate in blood plasma, and some of which are membrane bound. Some complement proteins bind, in an ordered sequence, to antigen-antibody complexes on target cells, facilitating cell lysis. Other complement proteins facilitate clearance of antibody-antigen complexes from the body, others prevent cell lysis or excessive inflammation, while peptide fragments of other complement proteins stimulate inflammation.

Particular proinflammatory activities of activated complement proteins (and their fragments) include: release of histamine and other vasoactive mediators from mast cells to increase permeability of the capillaries at an affected site; attracting polymorphonuclear leukocytes and macrophages to sites of inflammation and enhancing the activity thereof; lysis of gram negative bacteria, and damage to the membranes of many other types of targeted cells, including self cells, bearing foreign antigens; and facilitating adherence of leukocytes and macrophages to the surface of cells targeted for ingestion (such as bacteria and viruses, or self cells) via antigen-antibody complexes.

General interrelationships between the immune system, the complement system, and inflammatory conditions are well recognized in the art. For example, CD4+ T-cells are known to release lymphokines, such as λ-interferon, which stimulate macrophages to release substances that increase inflammation at an affected site, permitting destruction of invading pathogens. It is thus apparent that the inflammatory response, and cell mediated immune processes, reflect a complex set of interrelated mechanisms that permit response to injury, and infection. Unfortunately, the component pathways of this complex system occasionally work in ways adverse to the body, preventing appropriate response to disease states, or actually causing the disease states themselves. As a result, the specificity of the compounds of the invention contribute to their therapeutic value.

Particular inflammatory diseases that may be treated according to the practice of the invention include psoriasis, and inflammatory diseases of the gastrointestinal tract such as ulcerative colitis and Crohn's disease.

An additional category of inappropriate immune response includes those processes involving antibody-mediated (intermediate-type) hypersensitivity reactions (typically involving IgE antibodies), and which are often termed allergies. Generally speaking, allergy or hypersensitivity may be defined as an altered state, induced by an antigen, in which pathologic reactions can be subsequently elicited by exposure to that antigen, or to structurally similar substances. Representative examples include asthma, hay fever, hives, infantile eczema, atopic dermatitis, and gastrointestinal disturbances. Activated T-cells are also involved in these inappropriate immune responses.

(3) A considerable number of disease states involve circumstances where an individual produces antibodies and reactive T-cells against his or her own proteins or cells. Such circumstances are a significant exception to the general principle of self-tolerance, whereinby self-molecules do not trigger an immune response. A significant number of mechanisms are recognized whereinby an autoimmune response to a self-antigen can be triggered. Self-antigens may represent self-proteins that are denatured or otherwise modified after being produced on ribosomes, thus exposing novel epitopes (immune-recognized domains, typically short peptide or carbohydrate sequences) which are then taken up and processed by antigen-presenting cells and made available to receptive T-cells. Loss of thyroid function following chronic inflammation of the thyroid (Hashimoto's disease) may involve such an autoimmune pathway. Another thyroid pathology, thyroiditis followed by hyperthyroidism, may be explained by immune recognition of the cell surface receptor for thyroid stimulating hormone, however with the less typical result that antibody binding to the recognized cells results in their stimulation, not death.

Similarly, an autoimmune response may be mounted against an altered distribution of self-antigen. For example, self antigen from an organ may be exposed only after serious injury, and immune-mediated inflammation (see below) may then enhance and perpetuate the primary response. Persistent viral infections may also trigger autoimmune-like disease. It is not uncommon for host antibodies to bind to viral particles without neutralizing them, and it is possible that the resulting virus-antibody complexes may, over time, result in the production of what appear to be anti-self antibodies. Additionally, it is thought that certain T-cells termed Supressor Cells($T_s$) may act to suppress immune response to particular self-antigens. Defective production of such $T_s$ cells could permit activation of autoreactive T-cells whose action would need to be suppressed by therapeutic intervention.

Finally, many of the most widespread and serious autoimmune diseases may have their origin in the phenomenon of antigenic mimicry. The epitopes (immune-recognized domains) of antigens of infecting bacteria and viruses may bear considerable resemblance to similar structural motifs (for example peptide sequences) in mammalian proteins. Thus, an immune response intended to be specific against structural features of an invading pathogen may unfortunately also target identical or nearly identical macromolecular structural elements of self proteins.

Infections with some viruses are statistically associated with the onset of myasthenia gravis and insulin-dependent (juvenile/type I) diabetes. In type I diabetic disease, the panceatic beta (islet) cells that produce insulin are selectively destroyed. The human disease appears to depend on activated CD4+ T-cells and corrleates with the inherited presence in patients of specific HLA alleles (for example, DR3 or DR4 homozygotes, and DR4/DR3 heterozygotes have a high probability of contracting the disease). Although the exact beta cell autoantigen and autoantigen epitope(s) are unknown, homology with a Coxsackie B virus protein is suspected. It has been proposed that in susceptible individuals, having particular HLA alleles, presentation of viral antigen to T-cells unfortunately leads to cross-recognition of beta cell surface proteins by the immune system, with the result of gradual death of the entire beta cell population.

Thus, as the type I disease progresses, the patient becomes insulin dependent. However, diagnostic procedures for susceptibility to type I disease are known in the art, and the at-risk patient can be placed on a program of life-long immune suppression to prevent full onset of the autoimmune disease (thereby protecting surviving insulin-producing pancreatic cells). In those cases where no insulin producing cells survive (full type I disease), the disease may be treated by transplantation of pancreatic islet cells. In such case, the approach of the present invention is best characterized as prevention of transplant rejection.

The mechanisms of causation and progression for rheumatoid arthritis appear to share in-common features with those for type I diabetes. In rheumatoid arthritis, synovial membranes enclosing joint spaces are subject to very pronounced infiltration by lymphocytes, macrophages, and other cells. Compared to a control population, rheumatoid arthritis patients tend to express DR4, DR1, and DRw10 HLA haplotypes at high frequency. It is again likely that presentation of a self peptide by particular surface HLA molecules to receptive T-cells is essential to development of the disease. Consequently, suppression of resultant T-cell activation, and downstream signalling events, is an important strategy for therapeutic intervention. Additional autoimmune diseases that can be treated according to the practice of the invention include lupus (including systemic lupus erythematosus and lupus nephritis), pemphigus vulgaris (in which the recognized self-antigen is found in epidermal cells), thrombocytopenic purpura (in which the level of functional platelets falls to very low levels), and multiple sclerosis (wherein demyelinating activity may result from infection of the nervous system by a virus, bringing appropriate antigen in contact with T-cells).

The present invention provides highly specific inhibitors of T-cell Icktyrosine kinase. Administration of such compounds interferes with T-cell activation, and subsequent signalling events, thereby providing an effective means of intervention in the above-identified cell mediated immune responses.

The present invention also provides a method of treating or preventing T-cell leukemias, T-cell lymphomas, and other T-cell malignancies, whether the affected cells are primarily circulating or non-circulating. In this embodiment of the invention, it is not necessary that the involved T cells be activated.

The present invention also provides a method of treating the multifaceted pathology of Alzheimer's disease, and the complications thereof.

Pharmaceutical Formulations

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared, for example, by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., asthma) in the average adult human are preferably arranged so that each metered dose or "puff" of aerosol contains 20 µg to 1000 µg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

As is well recognized, the precise dose, and method and timing of administration thereof, are capable of determination by those skilled in the art, and depend upon numerous factors including the activity of the therapeutic compound, the properties of the formulation thereof, the nature and location of the target tissue, and the particulars of the disease state as it exists in a particular patient.

A compound of formula (I) administered in a pharmaceutically acceptable form either alone or in combination with one or more additional agents which modulate a mammlian immune system or with one or more anti-inflammatory agents. Such additional agents may include, but are not limited to, cyclosporin A (e.g. Sandimmune® or Neoral®), rapamycin, FK-506 (tacrolimus), leflunomide, CD40L Ab, methotrexate, FTY720, deoxyspergualin and analogs thereof, mycophenolate (e.g. Cellcept®), azathioprine (e.g. Imuran®), daclizumab (e.g. Zenapax®), OKT3 (e.g. Orthocolone®), AtGam, aspirin, acctaminophen, ibuprofen, naproxen, piroxicam, and antiinflmmatory steroids (e.g. prednisolone or dexamethasone). Such agents may be administered as part of the same or ofg separate dosage forms, via the same or different routes of administration, and on the same or different administration schedules according to standard pharmaceutical practice.

As examples, FK506 (Tacrolimus) may be given orally at 0.10–0.15 mg/kg body weight, every 12 hours, within first 48 hours postoperative, for example. Dose is monitored by measurement of serum Tacrolimus trough levels.

Cyclosporin A (Sandimmune® oral or intravenous formulation, or Neoral®, oral solution or capsules) may be given orally at 5 mg/kg body weight, every 12 hours within 48 hours postoperative. Dose is monitored by measurement of blood cyclosporin A trough levels.

The compounds of the present invention can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397. Additionally, the compounds of the present invention can be formulated using tehcnologies that provide continuous dosing via the digestive tract including, for example, osmotic systems, such as described in U.S. Pat. No. 4,612,008.

Synthesis of Compounds of the Invention

The following reaction schemes illustrate preparation of compounds of the present invention.

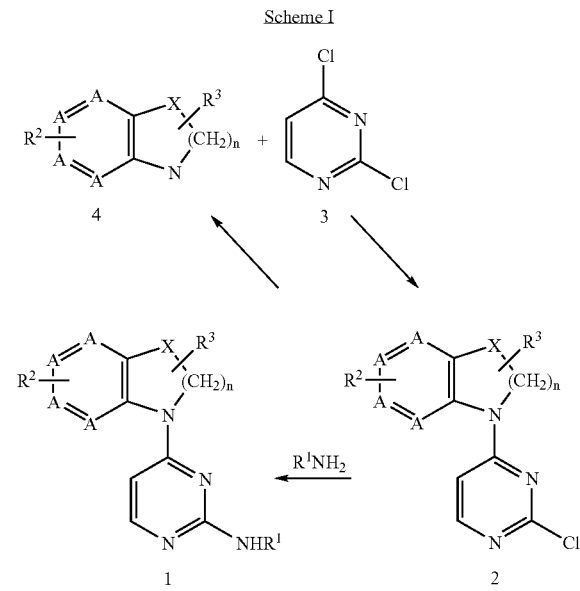

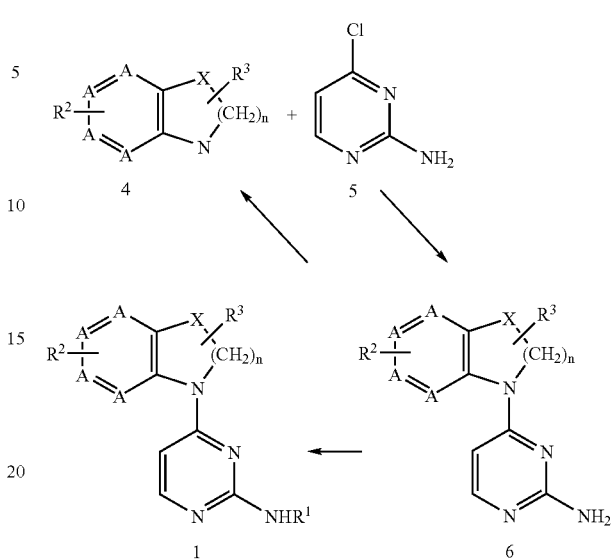

General Reaction Conditions

Generally speaking, the compounds of the invention are made in a two step process. First, the reactive nitrogen atom of compound 4 (indicated by an arrow above) preferentially displaces the 4-chloro group of 2,4-dichloropyrimidine (compound 3) under basic conditions to form compound 2. In a second step, generally in the presence of an acid catalyst, compound 2 is treated with an amine to form compound 1, wherein the amine nitrogen displaces the 2-chloro atom of the pyrimidine.

The reaction of compounds 4 and 3 is best conducted under basic conditions. Examples of suitable conditions include refluxing with a trialkylamine such as triethylamine in an alcohol solvent such as ethanol. As aforementioned, the 4-chloro group in 2,4-dichloropyrimidine is selectively displaced in the formation of compounds 2.

Subsequent treatment of compound 2 with an amine yields compound 1 as product. Selection of the appropriate amine is determined by the required structure of the product. The reaction solvent is chosen to both facilitate the solubility of the amine, and its subsequent reaction. For example, in the case of aniline or substituted anilines, the amine may be dissolved in an acetone/water solution in the presence of a catalytic amount of HCl, followed by heating for 18 hours at 50° C., for example. Mixtures of THF/water also provide combinations of solvent and reaction conditions that are generally useful. Conditions suited to reaction of any particular amine are readily determined.

Some compounds of the invention are made in a two step process shown in Scheme II where, in the first step, the reactive nitrogen of a compound 4 displaces the 4-chloro group of 2-amino-4-chloropyrimidine (compound 5) under basic conditions to form compound 6. In a second step, optionally in the presence of a tertiary amine base such as triethylamine, compound 6 is treated with a suitable agent, such as an acylating or sulfonylating agent to give compound 1. Examples of suitable acylating agents include, but are not limited to, acid chlorides, sulfonyl chlorides such as aryl or heteroarylsulfonyl chlorides, carbamoyl chlorides, chloroformates, and isocyanates, or a carboxylic acid in the presence of a suitable coupling agent such as a 1-(3-dimethylaminopropyl)-3-ethylcarbodiimide hydrochloride in a suitable solvent such as THF. In this regard, it is understood that the acylating agent is chosen to deliver $R^1$ according to the general formula I.

Both compound 3 (2,4-dichloropyrimidine) and compound 5 (2-amino-4-chloropyrimidine) are readily prepared and commercially available.

Compounds 4 are also readily prepared, or are commercially available, and may contain one or more optional substituents $R^2$, and one or more optional substituents $R^3$ (where it is understood that the $R^3$ group is attached to a ring carbon (including at X, if, X is a methylene group), as indicated below.

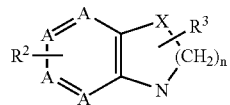

Representative ring structures for compound 4 include 1,2,3,4-tetrahydroquinoline; 1,2,3,4-tetrahydroquinoxaline; 3,4-Dihydro-1H-quinoxaline-2-one (2-oxo-1,2,3,4-tetrahydroquinoxaline); 3,4-Dihydro-2H-benzo[1,4]oxazine (3,4-2H-2H-benzo(1,4)oxazin-6-ol); 2,3-Dihydro-1H-indole; and 3,4-Dihydro-2H-benzo[1,4]thiazine, respectively, as shown below.

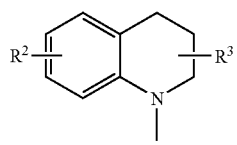
4a

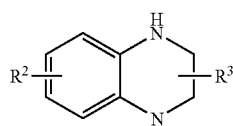
4b

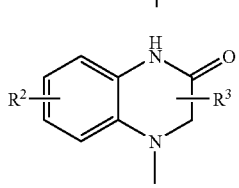
4c

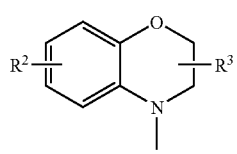
4d

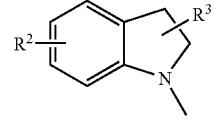
4e

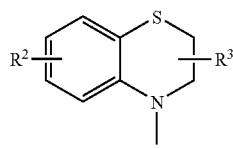
4f

Structures 4a to 4f above, for example, are commercially available where $R^2$ and $R^3$ are hydrogen. Additional species that are readily available in commerce include 7-methyl-1,2,3,4-tetrahydroquinoline; 6-methyl-1,2,3,4-tetrahydroquinoline; 5-methyl-1,2,3,4-tetrahydroquinoline; 6-methoxy-1,2,3,4-tetrahydroquinoline; 7-trifluoromethyl-1,2,3,4-tetrahydroquinoline; 6-fluoro-2-methyl-1,2,3,4-tetrahydroquinoline; 2-methyl-1,2,3,4-tetrahydroquinoline; 2,3-dihydro-1H-quinolin-4-one; 6-methoxy-2,3-dihydro-1H-quinolin-4-one; 2-methyl-2,3-dihydro-1H-indole; 2,3-dimethyl-2,3-dihydro-1H-indole; 5-fluoro-2,3-dihydro-1H-indole; 5-bromo-2,3-dihydro-1H-indole; 5-methanesulfinyl-2,3-dihydro-1H-indole; 5-methanesulfonyl-2,3-dihydro-1H-indole; and 2,3-dihydrobenzothiazole.

With respect to structures of type 4, additional synthetic approaches include the following:

(1) with respect to synthesis of the 2,3-dihydro-1H-indole ring system

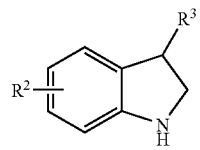

methods are disclosed in E. C. Taylor et al., *Tetrahedron*, 43, p. 5145 (1987).

(2) with respect to synthesis of the 3,4-Dihydro-1H-quinoxalin-2-one ring system

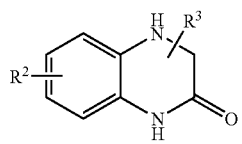

methods are disclosed in R. W. Holley, et al., J. A. Chem. Soc., 74, p. 3069, 1952 and R. E. TenBrink, *J. Med. Chem.* 37, p. 758, 1994;

(3) with respect to synthesis of the 1,2,3,4-tetrahydro-[1,5]naphthyridine ring system

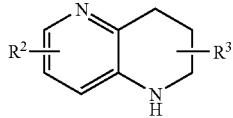

methods are disclosed in C. E. Neipp et al., *Tetrahedron Letters*, 38, p. 7499, 1997;

(4) with respect to synthesis of the 6,7,8,9-tetrahydro-5H-pyrido[2,3-b]azepine ring system

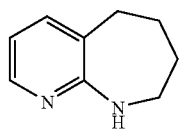

methods are disclosed in E. M. Hawes et al., *Tetrahedron*, 10, p. 39, 1973;

(5) with respect to synthesis of the 5,6,7,8-tetrahydropyrido{2,3-d]pyrimidine ring system,

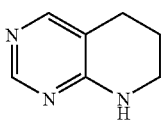

methods are disclosed in S. Kobayashi, Bull. Chem. Soc. Jpn., 46, p. 2835, 1973, and involve reaction of δ-valerolactam with formamide;

(6) with respect to synthesis of the 5,6,7,8-tetrahydropyrrolo{2,3-d]pyrimidine ring system;

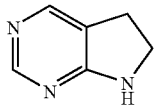

methods are disclosed in S. Kobayashi, Bull. Chem. Soc. Jpn., 46, p. 2835, 1973, and involve reaction of γ-butyrolactam with formamide;

(7) a large series of pyridopyridines are commercially available that can be reduced to the corresponding cyclic amines using known reduction methods including those cited in N. Ikekawa, et al., Chem. Pharm Bull., 6, p. 408, 1958; W. L. F. Armarego, J. Chem. Soc. (C), VIOL?, p. 377, 1967, and H. Rapoport et al., J. Org. Chem., 28, p. 1753, 1963. For example,

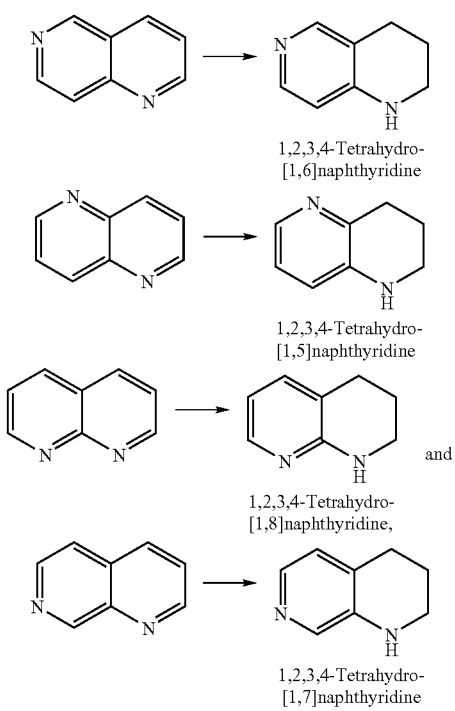

1,2,3,4-Tetrahydro-[1,6]naphthyridine 1,2,3,4-Tetrahydro-[1,5]naphthyridine 1,2,3,4-Tetrahydro-[1,8]naphthyridine, and 1,2,3,4-Tetrahydro-[1,7]naphthyridine (8) a large series of cyclic amides and diamides are commercially available that can be reduced with lithium aluminum hydride, or other suitable reducing agents as recognized in the art, to give the corresponding amines. For example,

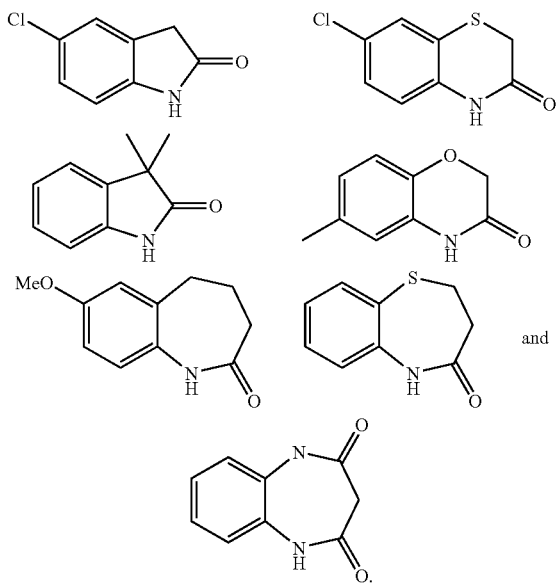

and

As aforementioned, preferred $R^2$ groups include halo, trifluoromethyl, ($C_1$–$C_6$)alkyl, hydroxy, ($C_1$–$C_6$)alkoxy-, and benzyloxy, for example, and compounds 4 in Schemes I and II containing them are commercially available or are readily synthesized.

Additionally, in the case where compound 4 is a 1,2,3,4-tetrahydroquinoxaline (4b), a ring nitrogen atom thereof may be substituted by ($C_1$–$C_6$)alkyl, ($C_1$–$C_6$)alkylsulfonyl, or phenylsulfonyl, and the like. In such cases it may be preferred to attach this substituent after the completion of all other chemistry, for example using an ($C_1$–$C_6$)alkylbromide, ($C_1$–$C_6$)alkylsulfonylchloride, or phenylsulfonylchloride.

The present invention is evidenced by the following examples.

EXAMPLES

Example 1

Preparation of 1-[(2-anilino)-4-pyrimidinyl]-6-methyl-1,2,3,4-tetrahydroquinoline 6-Methyl-1,2,3,4 tetrahydroquinoline (33.7 mmol) was added to a mixture of 2,4-dichloropyrimidine (33.5 mmol) and triethylamine (37 mmol) in EtOH (62 mL). The reaction mixture was refluxed for 3 h, cooled to room temperature, and the volatiles removed by rotary evaporation. The remaining solid was extracted with EtOAc/H$_2$O. The EtOAc layers were combined, dried over MgSO$_4$, filtered and the volatiles were then removed rotary evaporation. The residual solid was recrystallized from EtOAc/hexane to give compound 6, as depicted below, 1-(2-Chloro-pyrimidin-4-yl)-6-methyl-1,2,3,4-tetrahydroquinoline. [$^1$H-NMR (DMSO-d$_6$): 8.87 (d, J=6, 1H) 7.28 (d, J=8,1H) 7.04 (s, 1H) 7.00 (d, J=8, 1H) 6.93 (d, J=6, 1H) 3.79 (m, 2H) 2.65 (m, 2H) 1.85 (m, 2H); m/z 260 (M+1)] The 4-chloro group in 2,4-dichloropyrimidine was selectively displaced.

Subsequent treatment of compound 8 with the appropriate amine (in this case aniline) yields the product 7, in which the 2-chloro atom on the pyrimidine is replaced by the intended substituent. Aniline (0.173 mmol) was added to 1-(2-chloro-pyrimidin-4-yl)-6-methyl-1,2,3,4 tetrahyrdoquinoline (0.154 mmol) in 3 mL of acetone/water/ hydrochloric acid (10:15:0.2) and heated to 50° C. for 18 h. The reaction mixture was cooled to room temperature, and the precipitated solid was then filtered and recrystallized from ethyl acetate to give 1-[(2-anilino)-4-pyrimidinyl]-6-methyl-1,2, 3,4-tetrahydroquinoline [$^1$H-NMR (DMSO-$d_6$): 7.95 (d, J=8, 1H) 7.54 (d, J=8, 2H) 7.35 (m, 3H) 7.14 (m, 1H) 7.08 (m, 2H) 6.60 (d, J=8, 1H) 3.91 (m, 2H) 2.67 (m, 2H) 2.28 (s, 3H) 1.93 (m, 2H). m/z: 317(M+1)]

In Examples 2–8 below, synthetic procedures were very similar except for selection of the appropriate amine to react at the 2-chloro position of the pyrimidine ring.

Example 2

1-[2-[(4-bromophenyl)amino]-4-pyrimidinyl]-6-methyl-1,2,3,4-tetrahydroquinoline $^1$H-NMR(DMSO-$d_6$): 7.96 (d, J=7, 1H) 7.53 (m, 4H) 7.31 (d, J=8 1H) 7.09 (s, 1H) 7.07 (d, J=7 1H) 6.60 (d, J=8, 1H) 3.90 (m, 2H) 2.66 (m, 2H) 2.28 (s, 3H) 1.91 (m, 2H). m/z: 395,397(M+1)

Example 3

1-[2-[(4-methoxyphenyl)amino]-4-pyrimidinyl]-6-methyl-1,2,3,4-tetrahydroquinoline $^1$H-NMR(DMSO-$d_6$): 7.88 (b, 1H) 7.41 (d, J=8, 2H) 7.30 (d, J=8, 1H) 7.09 (s, 1H) 7.06 (d, J=8, 1H) 6.95 (d, J=8, 2H) 6.55 (d, J=8, 1H) 3.89 (m, 2H) 3.74 (s, 3H) 2.67 (m, 2H), 2.28 (s, 3H) 1.91 (m, 2H). m/z: 347(M+1)

Example 4

1-[2-[(1H-indazole-5-yl)]-4-pyrimidyl]-6-methyl-1, 2,3,4-tetrahydroquinoline $^1$H-NMR(DMSO-$d_6$): 9.11 (s, 1H) 8.17 (s, 1H) 7.95 (d, J=6, 1H) 7.84 ( s, 1H) 7.49 (d, J=8, 1H) 7.35 ( d, J=8, 1H) 7.27 ( d, J=8, 1H) 6.99 ( s, 1H) 6.96 ( d, J=8, 1H) 6.34 (d, J=7, 1H) 3.83 ( m, 2H) 2.64 (m,2H) 2.22 (s, 3H) 1.85 (m,2H). m/z: 357 (M+1)

Example 5

1-[2-[(4-phenoxyphenyl)amino]-4-pyrimidinyl]-6-methyl-1,2,3,4-tetrahydroquinoline $^1$H-NMR(DMSO-$d_6$): 9.20 (s, 1H) 7.94 (d, J=8, 1H) 7.71 (d, J=9 2H) 7.31 (m, 2H) 7.24 (d, J=8, 1H) 7.03 (t, J=8, 1H) 6.98 (s, 1H) 6.95 (d, J=8 1H) 6.90 (m, 4H) 6.37 (d, J=7, 1H) 3.83 (m, 2H) 2.64 (m, 2H) 2.22 (s, 3H) 1.85 (m, 2H). m/z: 409 (M=1)

Example 6

1-[2-[(3,4-dimethoxyphenyl)amino]-4-pyrimidinyl]-6-methyl-1,2,3,4-tetrahydroquinoline m/z: 377 (M+1)

Example 7

1-[2-[(3,4,5-trimethoxyphenyl)amino]-4-pyrimidinyl]-6-methyl-1,2,3,4-tetrahydroquinoline m/z: 407 (M+1)

Example 8

1-[2-[(4,N-phenylaminophenyl)amino]-4-pyrimidinyl]-6-methyl-1,2,3,4-tetrahydroquinoline m/z: 408 (M+1)

Example 9

[4-(6-Methyl-3,4-dihydro-2H-quinolin-1-yl)-pyrimidin-2-yl]-(6-morpholin-4-yl-pyridin-3-yl)-amine m/z 403 (M+1)

Example 10

5-[4-(6-Methyl-3,4-dihydro-2H-quinolin-1-yl)-pyrimidin-2-ylamino]-1,3-dihydro-benzoimidazol-2-one m/z 373 (M+1)

Example 11

(2,3-Dimethyl-1H-indol-5-yl)-[4-(6-methyl-3,4-dihydro-2H-quinolin-1-yl)-pyrimidin-2-yl]-amine m/z 384 (M+1)

Example 12

[4-(6-Methyl-3,4-dihydro-2H-quinolin-1-yl)-pyrimidin-2-yl-(2-methyl-2H-pyrazol-3-yl)-amine m/z 321 (M+1)

Example 13

(6-Methoxy-pyridin-3-yl)-[4-(6-methyl-3,4-dihydro-2H-quinolin-1-yl)-pyrimidin-2-yl]-amine m/z 348 (M+1)

Example 14

(4-Fluoro-3-methyl-phenyl)-[4-(6-methyl-3,4-dihydro-2H-quinolin-1-yl)-pyrimidin-2-yl]-amine m/z 349 (M+1)

Example 15

(5-Cyclopropyl-2H-pyrazol-3-yl)-[4-(6-methyl-3,4-dihydro-2H-quinolin-1-yl)-pyrimidin-2-yl]-amine m/z 347 (M+1)

Example 16

4-Benzyl-N % 3&-[4-(6-methyl-3,4-dihydro-2H-quinolin-1-yl)-pyrimidin-2-yl]-1H-pyrazole-3,5-diamine

Example 17

[4-(6-Methyl-3,4-dihydro-2H-quinolin-1-yl)-pyrimidin-2-yl]-(4-methyl-thiazol-2-yl)-amine m/z 338 (M+1)

Example 18

[4-(6-Methyl-3,4-dihydro-2H-quinolin-1-yl)-pyrimidin-2-yl]-(5-methyl-1H-pyrazol-3-yl)-amine m/z 321 (M+1)

The capability of the compounds of formula (I) to down-regulate immune system function is demonstrated by the following further examples.

Example 19

Short Term Whole Cell Assay for Compounds than Inhibit Ick, ZAP-70 and itk Enzymes The present assay measures interleukin-2 (IL-2) secreted from stimulated T-cells following binding to the cells (at the TcR) by known agonists, anti-CD3 and anti-CD28 antibodies. PTK-inhibitory compounds prevent downstream signalling and activation of the target cells by inhibiting phosphorylation of T-cell polypeptides that is necessary for the downstream signalling events (following binding to TcR) that otherwise result from antigen binding.

In the assay, Jurkat cells are incubated with candidate drug for one hour, and then stimulated with anti-CD3 and anti-CD28 antibodies provided on recoverable magnetic beads. After 18 hours of stimulation, cell supernatants are assayed for interleukin 2 by immunoassay. The following reagents are used in the assay:

(a) Dynabeads® M-450 coated with sheep-antimouse IgG (Dynal Co., product No. 110.02);

(b) anti-CD3 monoclonal antibody such as "OKT3", that is capable of signaling through the T-cell receptor complex when crosslinked;

(c) anti-CD28 monoclonal antibody, that is capable of signaling through the T-cell receptor complex when crosslinked;

(d) RPMI medium (Gibco);

(e) supplemented RPMI, to which 10% fetal calf serum, non essential amino acids (Gibco # 00467, final conc. is 1/100 that of stock), sufficient penicillin/streptomycin and, optionally, % (w/w) of L-glutamine have been added;

(f) human IL-2 assay kit, (R&D Systems, catalog No. D2050);

(g) dimethylsulfoxide (DMSO), Sigma Chemical Co., catalog No. D2650;

(h) 96 well flat bottom plates (Costar, catalog No. 3596); and (i) 96-well polypropylene plates (U-bottom, Costar Catalog No. 3365).

The Dynabeads® are prepared for assay by adding 6 micrograms of the anti-CD28 antibody and 120 micrograms of the anti-CD3 antibody to $4 \times 10^8$ beads, in a l ml volumne of Supplemented RPMI solution, followed by incubation for 1–3 hours at room temperature with gentle rocking. The fully complexed beads are then washed 3 times with 1 ml of RPMI medium, and then diluted to a bead density of $2.5 \times 10^7$/ml in supplemented RPMI. The beads may be stored at 4° C. It will be appreciated that the human CD3 and CD28 glycoprotein surface antigens have may epitopes against which monoclonal antibodies can be generated, and which possess sufficient affinity to permit proper running of the assay. Generally, it is preferred that the antibodies have a $K_A$ of about $10^{-8}$ or lower. Additional anti-human CD3 and anti-CD28 antibodies are known in the art, and/or are available for purchase.

Prior to assay, drug dilution plates must also be prepared. Test compounds are serially diluted (in triplicate) from 960 micromolar to 960 nanomolar on 96-well polypropylene plates using ½ log dilutions. The diluting solutions contain DMSO at concentrations appropriate to ensure that test compounds are maintained at 9.6% DMSO (v/v) during the dilutions. The assay itself is inhibited by DMSO and it is essential that concentration of DMSO be kept constant.

The test protocol is then as follows. In a typical assay, 5 microliters of test compound (the concentration range in the final dilution plates is between 960 micromolar and 960 nanomolar) is transfered from the final dilution plate to a Jurkat cell test plate (96-well flat bottom plate) which is brought up to 150 microliters final volume with Supplemented RPMI. At the resultant dilution of 1 to 30, the final DMSO concentration is 0.32% (v/v). $1.25 \times 10^5$ Jurkat cells are then added to each well (via 125 microliters of Supplemented RPMI medium containing the cells at a density therein of $1 \times 10^6$/ml). The cells are incubated with the test inhibitor compounds for 1 hour at 37° C.

Following this incubation, a 20 microliter quantity of the fully complexed bead suspension (at a bead density of $2.5 \times 10^7$/ml in supplemented RPMI) is added to each test well (as a result, $5 \times 10^5$ beads/well are used), and the incubation is continued for 18 hours at 37° C. The supernatants from each well are transferred to 96-well V-bottom plates in order to pellet the cells and beads. The supernatants are then assayed for interleukin-2 with the human IL-2 kit (R&D, #D2050) according to instructions contained therein.

The assay does not specifically discriminate between inhibition of T-cell activation caused by inhibition of Ick, ZAP-70 and itk PTK enzymes, or any combination thereof, but serves as a useful screen of promising compounds. Data are analyzed by polynomial regression and analzyed using a MACRO program. An $IC_{50}$ value of less than about 5 μM is preferred.

Example 20

Screen for Immunosuppressive Compounds that Inhibit the Kinase Activity of Ick Enzyme In the following assay, the potency of a test compound is determined as an $IC_{50}$ value, that is, the concentration of compound needed, under assay conditions, to inhibit 50% of Ick phosphorylation activity. In the present assay, the Ick substrate is "PGT", poly(glu-tyr) as sodium salt. The following reagents are used in the assay:

(a) DMSO (Sigma, catalog No. D2650);
(b) Dulbecco's medium diluted 1:1 with PBS (Sigma, catalog No.14190-136);
(c) Tween-20 detergent (Sigma, catalog No. P1379);
(d) bovine serum albumin (Sigma, catalog No. A-7030;
(e) ATP (Sigma, catalog No. A5394);
(f) PGT (Sigma, catalog No. P-0275);
(g) Nunc Maxisorp plates (Van Waters & Rogers, catalog No. 62409-004);
(h) lck-GST enzyme (a fusion protein of lck/glutathione—S-transferase, expressed from a Baculovirus vector system, and purified on a glutathione affinity column);
(i) plate coating buffer (100 µg/ml PGT in PBS);
(j) blocking buffer (3% bovine serum albumin in PBS);
(k) phosphorylation buffer (50 mM Hepes, pH 7.4, 125 mM NaCl, 24 mM $MgCl_2$);
(l) assay buffer (0.3 µM ATP in buffer (k));
(m) wash buffer (0.05% Tween-20 in PBS);
(n) for the detection antibody, the anti-phosphotyrosine antibody, PY-20, provided as a horseradish peroxidase ("HRP") conjugate (ICN catalog No. 69-151-1);
(o) TMB Microwell Peroxidase substrate (Kirkegaard and Perry, catalog No. 50-76-05);
(p) stop solution (0.09M $H_2SO_4$); and
(q) 96-well polypropylene plates (Costar, U-bottom, catalog No. 3365)

Serial Dilution of Test Compounds on Plates

The test compounds are solubilized in DMSO (100%) and brought to 10 mM as stock solutions. In this representative design, each 96-well polpyropylene drug dilution plate contains 3 compounds which are serially diluted 8 times, with a dilution factor of four for each dilution. The dilutions are performed in 50% DMSO, and set up such that each serial dilution is done in triplicate.

Prior to dilution 1, the test compound is present at 250 µM (prepared by adding 5 µl of 10 mM compound to 195 µl of 50% DMSO). From this point, consecutive four-fold dilutions are made. For example, dilution 2 is made by mixing 25 µl from dilution 1 with 75 µl of 50% DMSO, and dilution 3 is made by mixing 25 µl from dilution 2 with 75 µl DMSO, and the like. Thus, consecutive serial four-fold dilutions will be made at 250 µM, 62.5 µM, 15.6 µM, 3.9 µM, 0.98 µM, 0.24 µM, 0.06 µM, and 0.015 µM. Accordingly, for test compound 1, the consecutive serial dilutions proceed from wells A(1-3), to A(4-6), to A(7-9), to A(10-12), to B(1-3), to B(4-6), to B(7-9), to B(10-12). For test compound 2, consecutive serial dilutions proceed from wells C(1-3), to C(4-6), to C(7-9), to C(10-12), to D(4-6), to D(10-12), to E(1-3), to E(4-6). For test compound 3, consecutive serial dilutions proceed from wells E(7-9), to E(10-12), to F(1-3), to F(4-6), to F(7-9), to F(10-12), to G(1-3), to G(4-6). Additionally, wells D(1-3) and D(7-9) contain 50% DMSO only (no compound) and are used as positive and negative controls. All other wells on the plate, G(7-12) and H(1-12) are left unused. Then, an additional 25-fold dilution is accomplished when resultant test compound samples (5 µl) are transferred from the drug dilution plate to the assay plate wells (see below), each containing 120 µl of assay components. Thus, the concentrations of test compounds in the present assay are 10 µM, 2.5 µM, 0.625 µM, 0.156 µM, 0.039 µM, 0.0098 µM, 0.0024 µM, and 0.0006 µM. Following the above preparations, the assay itself is performed as follows.

The Maxisorp assay plates are coated with 100 µl of plate coating buffer, covered to prevent evaporation, and incubated overnight at 37° C. It should be noted that the concentration of PGT used is saturating. Following the overnight incubation, the assay plates are rinsed 3 times with wash buffer (350 µl/rinse).

From the test compound plate, 5 µl samples of test compound solution are added to the appropriate wells. Then 100 µl of assay buffer is added to each well (assay buffer is prepared by adding ATP to the phosphorylation buffer just prior to assay). Finally, an appropriate amount of LCK, determined by titration, is added to each well in a volume of 20 µl (generally, the LCK level should be near the top of the linear response range, i.e., about 80% thereof). The loaded assay plates are then shaken gently (covering is not necessary) at room temperature for 30 minutes, after which the plates are again washed three times with wash buffer.

To each plate well, 150 µl of blocking buffer is then added, and blocking is performed for 30 minutes at 37° C., during which time the plates are shaken and covered to prevent evaporation. The plates are again washed 3 times with wash buffer.

The detection antibody stock solution is then diluted 1:2000 in blocking buffer, and a 50 µl quantity thereof is added to each well, after which the plates are again shaken (at room temperature for 25 min), but with no covering needed. The procedure of washing the wells with wash buffer, three times, is repeated.

50 µl of TMB Microwell Peroxidase Substrate is then added to each well, and blue color is allowed to develop (about 1–5 minutes) until the OD value for the positive control (450 nm) is about 1.0. At this point, 50 µl of stop solution is added to each well and the plate is read on a plate reader (Softmax Pro) at 450 nm.

$IC_{50}$ values are determined by polynomial regression and analzyed using a MACRO program. An $IC_{50}$ value of less than about 3 µM is preferred.

What is claimed is:

1. A compound according to the formula

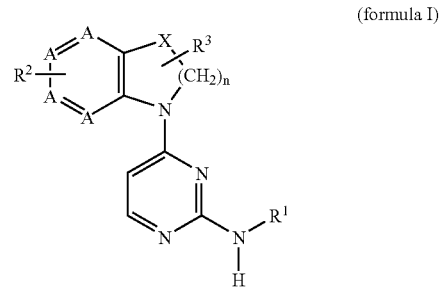

(formula I)

or pharmaceutically acceptable salts, solvates, or hydrates thereof; wherein each occurrence of A is independently selected from CH or N;

X is selected from the group consisting of —$CH_2$—, —O—, —NH—, ($C_1$–$C_6$)alkylamino-, ($C_1$–$C_6$) alkylaminocarbonylamino-, ($C_1$–$C_6$) alkylcarbonylamino-, ($C_1$–$C_6$)alkylsulfonylamino-, phenylsulfonylamino-, carbonyl, —NH—C(O)—, —N($C_1$–$C_6$)alkyl-C(O)—, —$S_y$— where y is 0, 1 or 2, and;

n in —$(CH_2)_n$— is 1, 2 or 3;

$R^1$ is phenyl, optionally substituted with one to five substituents, that are each independently selected from hydroxy-, halo-, amino-, ($C_1$–$C_6$)alkyl-, ($C_1$–$C_6$)

alkoxy-, trihalo($C_1$–$C_6$)alkyl-, ($C_1$–$C_6$)alkynl-, ($C_1$–$C_6$)alkylamino-, (($C_1$–$C_6$)$_2$)dialkylamino-, carboxy, ($C_1$–$C_6$)alkoxycarbonyl-, ($C_1$–$C_6$)acyloxy-, and ($C_1$–$C_6$)acylamino-wherein $R^4$ is selected from the groups consisting of (a) ($C_1$–$C_6$)alkyl-, ($C_2$–$C_6$)alkenyl-, or ($C_2$–$C_6$)alkynyl-, wherein the alkyl-, alkenyl- and alkynyl- groups are optionally substituted by hydroxy, halo, amino, trifluoromethyl, hydroxy($C_2$–$C_6$)alkyl-, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl(difluoromethylene)($C_1$–$C_3$)alkyl-, or nitro($C_1$–$C_6$)alkyl-;

(b) ($C_3$–$C_{10}$)cycloalkyl-, wherein the cycloalkyl- group is optionally substituted by hydroxy, halo, amino, trifluoromethyl, hydroxy($C_2$–$C_6$)alkyl-, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl(difluoromethylene)($C_1$–$C_3$)alkyl-, or nitro($C_1$–$C_6$)alkyl-; or (c) ($C_3$–$C_{10}$)heterocycloalkyl-, wherein the heterocycloalkyl- group is optionally substituted by hydroxy, halo, amino, trifluoromethyl, hydroxy($C_2$–$C_6$)alkyl-, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl(difluoromethylene)($C_{1-C3}$)alkyl-, or nitro($C_1$–$C_6$)alkyl-;

$R^2$ represents one to four optional substituents, each being independently selected from the members of groups (a) to (f)

(a) deuterium, halo, hydroxy, carboxy, amino, trifluoromethyl, ($C_1$–$C_6$) alkyl-, ($C_2$–$C_6$)alkenyl-, ($C_2$–$C_6$)alkynyl-, ($C_1$–$C_6$)alkylamino-, (($C_1$–$C_6$)(alkyl)$_2$amino-, cyanoalkyl-, ($C_3$–$C_{10}$)cycloalkyl, ($C_3$–$C_{10}$)heterocycloalkyl-, ($C_3$–$C_{10}$)cycloalkoxy-, ($C_1$–$C_6$)alkylthio-, ($C_1$–$C_6$)alkylsulfinyl-, ($C_1$–$C_6$)alkysulfonyl-, amino-CO—NH—, ($C_1$–$C_6$)alkoxy-CO—NH—, ($C_1$–$C_6$)alkyl-CO—NH—, ($C_1$–$C_6$)alkyl-CO—NH—($C_1$–$C_6$)alkyl, ($C_1$–$C_6$)alkyl-CO—NH—($C_1$–$C_6$)alkoxy-, ($C_1$–$C_6$)alkoxycarbonyl($C_1$–$C_6$)alkoxy-, ($C_1$–$C_6$)alkoxy-CO—NH—($C_1$–$C_6$)alkoxy-, ($C_1$–$C_6$)alkylamino-CO—NH—, ($C_1$–$C_6$)alkylamino-CO—NH—($C_1$–$C_6$)alkyl, (($C_1$–$C_6$)alkyl)$_2$amino-CO—NH—($C_1$–$C_6$)alkyl, (($C_1$–$C_6$)alkyl)$_2$amino-CO—NH-carboxy, carboxy($C_1$–$C_6$)alkyl-, carboxy ($C_1$–$C_6$)alkoxy-, benzyloxycarbony($C_1$–$C_6$)alkoxy-, ($C_1$–$C_6$)alkylamino-CO—, ($C_1$–$C_6$)acylamino-, ($C_1$–$C_6$)alkoxy-, ($_1$–C6)acyl-, ($C_1$–$C_6$)acyloxy-, ($C_1$–$C_6$)acyl($C_1$–$C_6$)alkylamino-, ($C_1$–$C_6$)alkoxyacyl-, ($C_1$–$C_6$)alkylaminoacyl-, (($C_1$–$C_6$)alkyl)$_2$aminoacyl-, amino($C_1$–$C_6$)acyl-, amino($C_1$–$C_6$)alkyl-, ($C_1$–$C_6$)alkoxycarbonylamino-, ($C_1$–$C_6$)alkoxycarbonyl ($C_1$–$C_6$)alkyl-, ($C_6$–$C_{10}$)aryl($C_1$–$C_6$)alkoxycarbonylamino, trihalomethyl-, trihalomethyl ($C_1$–$C_6$)alkyl-, ($C_1$–$C_6$)alkyldihalomethylene-, ($C_1$–$C_3$)alkyl(dihalomethylene)($C_1$–$C_3$)alkyl-, ($C_3$–$C_6$)cycloalkyl-, ($C_3$–$C_6$)cycloalkyl($C_1$–$C_6$)alkyl-, hydroxy ($C_1$–$C_6$)alkyl-, ($C_1$–$C_6$)acyloxy($C_1$–$C_6$)alkyl-, ($C_1$–$C_6$)alkoxy($C_1$–$C_6$)alkyl-, ($C_1$–$C_6$)acylamino($C_1$–$C_6$)alkyl-, ($C_1$–$C_6$)alkylthio($C_1$–$C_6$)alkyl-, ($C_1$–$C_6$)alkoxycarbonyl-, ($C_1$–$C_6$)alkylsulfinyl($C_1$–$C_6$)alkyl-($C_1$–$C_6$)alkylsulfonyl($C_1$–$C_6$)alkyl-, ($C_1$–$C_6$)alkylsulfonyl-, ($C_1$–$C_6$)alkylsulfonylamino-, ($C_1$–$C_6$)alkylsulfonylamino($C_1$–$C_6$)alkyl-, amino($C_1$–$C_6$)alkyl-, ($C_1$–$C_6$)alkylamino($C_1$–$C_6$)alkyl-, (($C_1$–$C_6$)alkyl$_2$amino($C_1$–$C_6$)alkyl-, ($C_1$–$C_6$)CO($C_1$–$C_6$)alkyl-;

(b) ($C_6$–$C_{10}$)aryl-, ($C_1$–$C_9$)heteroaryl-, ($C_6$–$C_{10}$)aryl($C_6$–$C_{10}$)aryl($C_1$–$C_9$)heteroaryl-, ($C_1$–$C_9$)heteroaryl($C_1$–$C_9$)heteroaryl-, ($C_1$–$C_9$)heteroaryl($C_6$–$C_{10}$)aryl-, ($C_6$–$C_{10}$)arylsulfinyl-, ($C_6$–$C_{10}$)aryl($C_6$–$C_{10}$)arylsulfinyl-, ($C_1$–$C_9$)heteroaryl($C_6$–$C_{10}$)arylsulfinyl-, ($C_6$–$C_{10}$)arylsulfonyl-, ($C_6$–$C_{10}$)aryl($C_6$–$C_{10}$)arylsulfonyl-, ($C_1$–$C_9$)heteroaryl($C_6$–$C_{10}$)arylsulfonyl-, ($C_1$–$C_9$)heteroarylsulfinyl-, ($C_1$–$C_9$)heteroaryl($C_1$–$C_9$)heteroarylsulfinyl-, ($C_6$–$C_{10}$)aryl($C_1$–$C_9$)heteroarylsulfinyl-, ($C_1$–$C_9$)heteroarylsulfonyl-, ($C_1$–$C_9$)heteroaryl($C_1$–$C_9$)heteroarylsulfonyl-, ($C_6$–$C_{10}$)aryl($C_1$–$C_9$)heteroarylsulfonyl-, ($R^4$)sulfinyl-, ($R^4$)sulfonyl-, ($C_6$–$C_{10}$)aryl($R^4$)sulfinyl-, ($C_6$–$C_{10}$)aryl($C_6$–$C_{10}$)aryl($R^4$)sulfinyl-, ($C_1$–$C_9$)heteroaryl($C_6$–$C_{10}$)aryl($R^4$)sulfinyl-, ($C_6$–$C_{10}$)aryl($R^4$)sulfonyl-, ($C_6$–$C_{10}$)axyl($C_6$–$C_{10}$)aryl($R^4$)sulfonyl-, ($C_1$–$C_9$)heteroaryl($C_6$–$C_{10}$)aryl($R^4$)sulfonyl-, ($C_1$–$C_9$)heteroaryl($R^4$)sulfinyl, ($C_6$–$C_{10}$)aryl($C_1$–$C_9$)heteroaryl($R^4$)sulfinyl-, ($C_1$–$C_9$)heteroaryl($C_1$–$C_9$)heteroaryl($R^4$)sulfinyl-, ($C_1$–$C_9$)heteroaryl($R^4$)sulfonyl-, ($C_6$–$C_{10}$)aryl($C_5$–$C_9$)heteroaryl($R^4$)sulfonyl-, ($C_1$–$C_9$)heteroaryl($C_1$–$C_9$)heteroaryl($R^4$)sulfonyl-, ($C_6$–$C_{10}$)arylaminocarbonyl-, ($C_6$–$C_1$ O)aryl($C_6$–$C_{10}$)arylaminocarbonyl-, ($C_1$–$C_9$)heteroaryl($C_6$–$C_{10}$)arylaminocarbonyl-, ($C_1$–$C_9$)heteroarylaminocarbonyl-, ($C_6$–$C_{10}$)aryl($C_1$–$C_9$)heteroarylaminocarbonyl-, ($C_1$–$C_9$)heteroaryl($C_1$–$C_9$)heteroarylaminocarbonyl-, ($C_6$–$C_{10}$)arylcarbonyl-, ($C_6$–$C_{10}$)aryl($C_6$–$C_{10}$)arylcarbonyl-, ($C_1$–$C_9$)heteroaryl($C_6$–$C_{10}$)arylcarbonyl-, ($C_1$–$C9$)heteroarylcarbonyl-, ($C_6$–$C_{10}$)aryl($C_1$–$C_9$)heteroarylcarbonyl-, ($C_1$–$C_9$)heteroaryl($C_1$–$C_9$)heteroarylcarbonyl-, ($C_6$–$C_{10}$)aryloxycarbonyl-, ($C_6$–$C_{10}$)aryl($C_6$–$C_{10}$)aryloxycarbonyl-, ($C_1$–$C_9$)heteroaryl($C_6$–$C_{10}$)aryloxycarbonyl-, ($C_1$–$C_9$)heteroaryloxycarbonyl-, ($C_6$–$C_{10}$)aryl($C_1$–$C_9$)heteroaryloxycarbonyl-, ($C_1$–$C_9$)heteroaryl($C_1$–$C_9$)heteroaryloxycarbonyl-, ($R^4$)carbonyl-, ($R^4$)oxycarbonyl-, ($R^4$)aminocarbonyl-, ($C_6$–$C_{10}$)aryl($R^4$)carbonyl-, ($C_6$–$C_{10}$)aryl($R^4$)oxycarbonyl-, ($C_6$–$C_{10}$)aryl($R^4$)aminocarbonyl-, ($C_1$–$C_9$)heteoaryl($R^4$)carbonyl-, ($C_5$–$C_9$)heteroaryl($R^4$)oxycarbonyl-, ($C_1$–$C_9$)heteroaryl($R^4$)aminocarbonyl-, wherein $R^4$ is defined as above, and wherein any of said of ($C_6$–$C_{10}$)aryl- or ($C_1$–$C_9$)heteroaryl- $R^2$ groups may be optionally substituted by one to five groups independently selected from:

(i) hydroxy, halo, amino, trifluoromethyl, carboxy, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, or nitro($C_1$–$C_6$)alkyl-, ($C_1$–$C_3$)alkyl(difluoromethylene)($C_1$–$C_3$)alkyl-, ($C_1$–$C_6$)acylamino($C_1$–$C_6$)alkyl-, ($C_1$–$C_6$)alkoxy($C_1$–$C_6$)acylamino-, amino($C_1$–$C_6$)acyl-, amino($C_1$–$C_6$)acyl($C_1$–$C_6$)alkyl-, ($C_1$–$C_6$)alkylamino($C_1$–$C_6$)acyl-, (($C_1$–$C_6$)alkyl)$_2$amino ($C_1$–$C_6$)acyl-, ($C_3$–$C_{10}$)cycloalkyl($C_1$–$C_6$)alkyl-, ($C_1$–$C_6$)acyloxy($C_1$–$C_6$)alkyl-, ($C_2$–$C_6$)alkoxy($C_1$–$C_6$)alkyl-, piperazinyl($C_1$–$C_6$)alkyl-, ($C_1$–$C_6$)acylamino($C_1$–$C_6$)alkyl-, ($C_6$–$C_{10}$)aryl($C_1$–$C_6$)alkoxy($C_1$–$C_6$)alkyl-, ($C_1$–$C_9$)heteroaryl($C_1$–$C_6$)alkoxy($C_1$–$C_6$)alkyl-, ($C_1$–$C_6$)alkylthio($C_1$–$C_6$)alkyl-, ($C_6$–$C_{10}$)arylthio($C_1$–$C_6$)alkyl-, ($C_1$–$C_6$)alkylsulfinyl($C_1$–$C_6$)alkyl-, ($C_6$–$C_{10}$)arylsulfinyl($C_1$–$C_6$)alkyl-, ($C_1$–$C_6$)alkylsulfonyl($C_1$–$C_6$)alkyl-, ($C_6$–$C_{10}$)arylsulfonyl($C_1$–$C_6$)alkyl-, amino($C_1$–$C_6$)alkyl-, ($C_1$–$C_6$)alkylamino($C_1$–$C_6$)alkyl-, ($C_1$–$C_6$)alkyl(difluoromethylene)-, ($C_1$–$C_3$)alkyl(difluoromethylene)($C_1$–$C_3$)alkyl-, ($C_1$–$C_6$)alkoxy($C_1$–$C_6$)acyl-, ($C_1$–$C_6$)alkylamino($C_1$–$C_6$)acyl-, (($C_1$–$C_6$)alkyl)$_2$amino($C_1$–$C_6$)acyl- ($C_6$–$C_{10}$)aryl-, ($C_1$–$C_9$)heteroaryl-, ($C_6$–$C_{10}$)aryl($C_1$–$C_6$)alkyl-, ($C_1$–$C_9$)heteroaryl($C_1$–$C_6$)alkyl-, ($C_6$–$C_{10}$)aryl($C_6$–$C_{10}$)aryl-, ($C_6$–$C_{10}$)aryl($C_6$–$C_{10}$)aryl($C_1$–$C_6$)alkyl-, ($C_3$–$C_{10}$)cycloalkyl-, ($C_3$–$C_{10}$)cycloalkyl($C_1$–$C_6$)alkyl-, ($C_3$–$C_{10}$)heterocycloalkyl-, ($C_3$–$C_{10}$)heterocycloalkyl($C_1$–$C_6$)alkyl-, hydroxy($C_2$–$C_6$)alkyl-, ($C_1$–$C_6$)acyloxy($C_2$–$C_6$)alkyl-, ($C_1$–$C_6$)alkoxy($C_2$–$C_6$)alkyl-, piperazinyl($C_1$–$C_6$)alkyl-, ($C_1$–$C_6$)acylamino($C_1$–$C_6$)alkyl-, ($C_6$–$C_{10}$)aryl($C_1$–$C_6$)alkoxy($C_1$–$C_6$)alkyl-, ($C_1$–$C_9$)heteroaryl($C_1$–$C_6$)alkoxy($C_1$–$C_6$)alkyl-, ($C_1$–$C_6$)alkylthio($C_1$–$C_6$)alkyl-, ($C_6$–$C_{10}$)arylthio($C_1$–$C_6$)alkyl-, ($C_1$–$C_6$)alkylsulfinyl($C_1$–$C_6$)alkyl-, ($C_6$–$C_{10}$)arylsulfinyl($C_1$–$C_6$)alkyl-, ($C_1$–$C_6$)alkylsulfonyl($C_1$–$C_6$)alkyl-, ($C_6$–$C_{10}$)axylsulfonyl($C_1$–$C_6$)alkyl-, amino($C_1$–$C_6$)alkyl-, ($C_1$–$C_6$)alkylamino($C_1$–$C_6$)alkyl-, (($C_1$–$C_6$)alkyl)$_2$amino($C_1$–$C_6$)alkyl-;

(ii) $R^5OCO(C_1$–$C_6)$alkyl- wherein $R^5$ is selected from the group consisting of hydrogen, ($C_1$–$C_6$)alkyl, ($C_6$–$C_{10}$)aryl($C_1$–$C_6$)alkyl-, ($C_1$–$C_9$)heteroaryl($C_1$–$C_6$)alkyl-;

(iii) $R^6(C_2$–$C_6)$alkyl- wherein $R^6$ is selected from the group consisting of piperazino, ($C_1$–$C_6$)acylpiperazino-, ($C_6$–$C_{10}$)arylpiperazino-, ($C_5$–$C_9$)heteroarylpiperazino-, ($C_1$–$C_6$)alkylpiperazino-, ($C_6$–$C_{10}$)aryl($C_1$–$C_6$)alkylpiperazino-, ($C_1$–$C_9$)heteroaryl($C_1$–$C_6$)alkylpiperazino-, morpholino-, ($C_1$–$C_6$)acylmorpholino-, ($C_6$–$C_{10}$)arylmorpholino-, ($C_1$–$C_9$)heteroarylmorpholino-, ($C_1$–$C_6$)alkylmorpholino-, ($C_6$–$C_{10}$)aryl($C_1$–$C_6$)alkylmorpholino-, ($C_1$–$C_9$)heteroaryl($C_1$–$C_6$)alkylmorpholino-, thiomorpholino-, ($C_1$–$C_6$)acylthiomorpholino-, ($C_6$–$C_{10}$)arylthiomorpholino-, ($C_1$–$C_9$)heteroarylthiomorpholino-, ($C_1$–$C_6$)alkylthiomorpholino-, ($C_6$–$C_{10}$)aryl($C_1$–$C_6$)alkylthiomorpholino-, ($C_1$–$C_9$)heteroaryl($C_1$–$C_6$)alkylthiomorpholino-, piperidino-, ($C_1$–$C_6$)acylpiperidino-, ($C_6$–$C_{10}$)arylpiperidino-, ($C_1$–$C_9$)heteroarylpiperidino-, ($C_1$–$C_6$)alkyl piperidino-, ($C_6$–$C_{10}$)aryl($C_1$–$C_6$)piperidino-, ($C_1$–$C_9$)heteroaryl($C_1$–$C_6$)alkylpiperidino-, pyrrolidino-, ($C_1$–$C_6$)acylpyrrolidino-, ($C_6$–$C_{10}$)arylpyrrolidino-, ($C_1$–$C_9$)heteroarylpyrrolidino-, ($C_1$–$C_6$)alkylpyrrolidino-, ($C_6$–$C_{10}$)aryl($C_1$–$C_6$)alkylpyrrolidino-, ($C_1$–$C_9$)heteroaryl($C_1$–$C_6$)alkylpyrrolidino-, ($C_1$–$C_6$)alkoxy($C_1$–$C_6$)acyl-, ($C_1$–$C_6$)alkylamino($C_6$–$C_{10}$)aryl-, and (($C_1$–$C_6$)alkyl$_2$amino($C_1$–$C_6$)acyl-;

(c) $R^7$, or $R^7Y$-, where $R^7$ is selected from the group consisting of piperazino-, ($C_6$–$C_{10}$)arylpiperazino-, ($C_1$–$C_9$)heteroarylpiperazino-, ($C_1$–$C_6$)alkylpiperazino-, ($C_6$–$C_{10}$)aryl($C_1$–$C_6$)alkylpiperazino-, ($C_1$–$C_9$)heteroaryl($C_1C_6$)alkylpiperazino-, morpholino-, ($C_6$–$C_{10}$)arylmorpholino-, ($C_1$–$C_9$)heteroarylmorpholino-, ($C_1$–$C_6$)alkylmorpholino-, ($C_6$–

$R^2$ represents one to four optional substituents, each being independently selected from the members of groups (a) to (f)

(a) deuterium, halo, hydroxy, carboxy, amino, trifluoromethyl, ($C_1$–$C_6$) alkyl-, ($C_2$–$C_6$)alkenyl-, ($C_2$–$C_6$)alkynyl-, ($C_1$–$C_6$)alkylamino-, (($C_1$–$C_6$)(alkyl)$_2$amino-, cyanoalkyl-, ($C_3$–$C_{10}$)cycloalkyl, ($C_3$–$C_{10}$)heterocycloalkyl-, ($C_3$–$C_{10}$)cycloalkoxy-, ($C_1$–$C_6$)alkylthio-, ($C_1$–$C_6$)alkylsulfinyl-, ($C_1$–$C_6$)alkylsulfonyl-, amino-CO—NH—, ($C_1$–$C_6$)alkoxy-CO—NH—, ($C_1$–

(b) ($C_3$–$C_{10}$)cycloalkyl-, wherein the cycloalkyl- group is optionally substituted by hydroxy, halo, amino, trifluoromethyl, hydroxy($C_2$–$C_6$)alkyl-, ($C_1$–$C_6$) alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl(difluoromethylene)($C_1$–$C_3$)alkyl-, or nitro($C_1$–$C_6$)alkyl-; or (c) ($C_3$–$C_{10}$)heterocycloalkyl-, wherein the heterocycloalkyl- group is optionally substituted by hydroxy, halo, amino, trifluoromethyl, hydroxy($C_2$–$C_6$) alkyl-, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl(difluoromethylene)($C_1$–$C_3$)alkyl-, or nitro($C_1$–$C_6$)alkyl-; $C_{10}$)aryl($C_1$–$C_6$)alkylmorpholino-, ($C_1$–$C_9$)heteroaryl($C_1$–$C_6$)alkylmorpholino-, thiomorpholino-, ($C_6$–$C_{10}$)arylthiomorpholino-, ($C_1$–$C_9$)heteroarylthiomorpholino-, ($C_1$–$C_6$)alkylthiomorpholino-, ($C_6$–$C_{10}$)aryl($C_1$–$C_6$)alkylthiomorpholino-, ($C_1$–$C_9$)heteroaryl($C_1$–$C_6$)alkylthiomorpholino-, piperidino-, ($C_6$–$C_{10}$)arylthiopiperidino-, ($C_1$–$C_9$)heteroarylthiopiperidino-, ($C_1$–$C_6$)alkylthiopiperidino-, ($C_6$–$C_{10}$)aryl($C_1$–$C_6$)alkylthiopiperdino-, ($C_1$–$C_9$)heteroaryl($C_1$–$C_6$)alkylthiopipendino-, pyrolidino-, ($C_6$–$C_{10}$)arylthiopyrolidino-, ($C_1$–$C_9$)heteroalylthiopyrolidino-, ($C_1$–$C_6$)alkylthiopyrolidino-, ($C_6$–$C_{10}$)aryl($C_1$–$C_6$)alkylthiopyrolidino-, ($C_1$–$C_9$)heteroaryl($C_1$–$C_6$)alkylthiopyrolidino-, and Y, if present, is selected from the group consisting of ($C_1$–$C_6$)alkyl-, ($C_2$–$C_6$)alkenyl-, ($C_2$–$C_6$)alkynyl-, amino, oxygen, thio, sulfinyl, sulfonyl, halo($C_2$–$C_6$)alkyl-, and hydroxy($C_2$–$C_6$)alkyl-;

(d) $ZR^8$—, where $R^8$ is selected from the group consisting of piperazino-, ($C_6$–$C_{10}$)arylpiperazino-, ($C_1$–$C_9$)heteroarylpiperazino-, ($C_1$–$C_6$)alkylpiperazino-, ($C_6$–$C_{10}$)aryl($C_1$–$C_6$)alkylpiperazino-, ($C_1$–$C_9$)heteroaryl($C_1$–$C_6$)alkylpiperazino-, morpholino-, ($C_6$–$C_{10}$)arylmorpholino-, ($C_1$–$C_9$)heteroarylmorpholino-, ($C_1$–$C_6$)alkylmorpholino-, ($C_6$–$C_{10}$)aryl($C_1$–$C_6$)alkylmorpholino-, ($C_1$–$C_9$)heteroaryl($C_1$–$C_6$)alkylmorpholino-, thiomorpholino-, ($C_6$–$C_{10}$)arylthiomorpholino-, ($C_1$–$C_9$)heteroarylthiomorpholino-, ($C_1$–$C_6$)alkylthiomorpholino-, ($C_6$–$C_{10}$)aryl($C_1$–$C_6$)alkylthiomorpholino-, ($C_1$–$C_9$)heteroaryl($C_1$–$C_6$)alkylthiomorpholino-, piperidino-, ($C_6$–$C_{10}$)arylthiopiperidino-, ($C_1$–$C_9$)heteroarylthiopiperidino-, ($C_1$–$C_6$)alkylthiopiperidino-, ($C_6$–$C_{10}$)aryl($C_1$–$C_6$) alkylthiopiperidino-, ($C_1$–$C_9$)heteroaryl($C_1$–$C_6$) alkylthiopiperidino-, pyrolidino ($C_6$–$C_{10}$) arylthiopyrolidino-, ($C_1$–$C_9$)heteroarylthiopyrolidino-, ($C_1$–$C_6$)alkylthiopyrolidino-, ($C_6$–$C_{10}$)aryl($C_1$–$C_6$) alkylthiopyrolidino-, ($C_1$–$C_9$)heteroaryl($C_{1-C6}$) alkylthiopyrolidino, and Z is selected from the group consisting of ($C_1$–$C_6$)alkyl-, ($C_2$–$C_6$)alkenyl-, ($C_2$–$C_6$) alkynyl-, amino, oxygen, thio, sulfinyl, sulfonyl, halo ($C_1$–$C_6$)alkyl-, and hydroxy($C_2$–$C_6$)alkyl-;

(e) two or more of $R^2$, when vicinal, together to form one or more further rings of 4, 5, 6 or 7 member atoms selected from the group consisting of phenyl-, naphthyl-, furyl-, thienyl-, thiazolyl-, pyrazolyl-, isothiazolyl-, oxazolyl-, isoxazolyl-, pyrrolyl-, triazolyl-, tetrazolyl-, imidazolyl-, 1,3,5-oxadiazolyl-, 1,2,4-oxadiazolyl-, 1,2,3-oxadiazolyl-, 1,3,5-thiadiazolyl-,-1,2,3-thiadiazolyl-, 1,2,4-thiadiazolyl-, pyridyl-, pyrimidyl-, pyrazinyl-, pyridazinyl-, 1,2,4-triazinyl-, 1,2,3-triazinyl-, 1,3,5-triazinyl-, pyrazolo[3,4-b]pyridinyl-, cinnolinyl-, pteridinyl-, purinyl-, 6,7-dihydro-5H-[1]pyrindinyl-, benzo[b]thiophenyl-, 5, 6, 7, 8-tetrahydro-quinolin-3-yl, benzoxazolyl-, benzothiazolyl-, benzisothiazolyl-, benzisoxazolyl-, benzimidazolyl-, thianaphthenyl-, isothianaphthenyl-, benzofuranyl-, isobenzofuranyl-, isoindolyl-, indolyl-, indolizinyl-, indazolyl-, isoquinolyl-, quinolyl-, phthalazinyl-, quinoxalinyl-, quinazolinyl-, benzoxazinyl-, and wherein said ring(s) are optionally substituted by one or more ($C_1$–$C_6$)alkyl-, ($C_2$–$C_6$) alkenyl-, ($C_2$–$C_6$)alkynyl-, amino-, halo-, hydroxy-, carboxy-, thiol-, nitro-, cyano-, sulfonic-, halo($C_1$–$C_6$) alkyl-, and hydroxy($C_2$–$C_6$)alkyl-; and (f) two or more of $R^2$ when vicinal, together to form one or more further rings of 3, 4, 5, 6 or 7 member atoms selected from the groups consisting of:

(i) ($C_3$–$C_{10}$)cycloalkyl-, containing zero to two levels of unsaturation, selected from the group consisting of cyclopropyl-, cyclobutyl-, cyclopentyl-, cyclohexyl-, cycloheptyl-, cyclopropenyl-, cyclobutenyl-, cyclopentenyl-, cyclohexenyl-, cycloheptenyl-, 1,3-cyclobutadienyl-, 1,3-cyclopentadienyl-, 1,3-cyclohexadienyl-, 1,4-cyclohexadienyl-, 1,3-cycloheptadienyl-, 1,4-cycloheptadienyl-, bicyclo[3.2.1]octane-, bicyclo[2.2.1]heptane, the norborn-2-ene unsaturated form thereof, wherein said ring is optionally substituted by hydroxy-, halo-, amino-, trifluoromethyl-, hydroxy ($C_2$–$C_6$)alkyl-, ($C_1$–$C_6$)alkoxy-,($C_1$–$C_6$)acyloxy-, ($C_1$–$C_6$)alkylamino-, (($C_1$–$C_6$)alkyl)$_2$amino-, ($C_1$–$C_6$)acylamino-, cyano-, nitro-, carboxy-, thiol-, sulfonyl-, ($C_1$–$C_6$)alkyl-, ($C_2$–$C_6$)alkenyl-, ($C_2$–$C_6$) alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl (difluoromethylene)($C_1$–$C_3$)alkyl-, halo($C_1$–$C_6$) alkyl- or nitro($C_1$–$C_6$)alkyl-; and (ii) ($C_3$–$C_{10}$)heterocycloalkyl- selected from the group consisting of pyrrolidinyl-, tetrahydrofuranyl-, dihydrofuranyl-, tetrahydropyranyl-, pyranyl-, thiopyrany-1, aziridinyl-, oxiranyl-, methylenedioxyl-, isoxazolidinyl,- 1,3-oxazolidin-3-yl-, isothiazolidinyl-, 1,3-thiazolidin-3-yl-, 1,2-pyrazolidin-2-yl-, 1,3-pyrazolidin-1-yl-, piperidinyl-, thiomorpholinyl-, 1,2-tetrahydrothiazin-2-yl-, 1,3-tetrahydrothiazin-3-yl-, tetrahydrothiadiazinyl-, morpholinyl-, 1,2-tetrahydrodiazin-2-yl-, 1,3-tetrahydrodiazin-1-yl-, tetrahydroazepinyl-, piperazinyl-, chromenyl-, chromanyl-, where said ring is optionally substituted by hydroxy-, halo-, amino-, trifluoromethyl-, hydroxy($C_2$–$C_6$)alkyl-, ($C_1$–$C_6$)alkoxy-, ($C_1$–$C_6$) acyloxy-, ($C_1$–$C_6$)alkylamino-, cyano-, nitro-, carboxy-, thiol-, sulfonyl-, ($C_1$–$C_6$)alkyl-, ($C_2$–$C_6$) alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, ($C_1$–$C_3$)alkyl(difluoromethylene)($C_1$–$C_3$)alkyl-, halo($C_1$–$C_6$)alkyl or nitro($C_1$–$C_6$)alkyl-; wherein any ($C_1$–$C_6$)alkyl-, ($C_2$–$C_6$)alkenyl-, ($C_2$–$C_6$) alkynyl-, ($C_3$–$C_{10}$)cycloalkyl- or ($C_3$–$C_{10}$) heterocycloalkyl- groups that are, or comprise a portion of, said one to four optional $R^2$ substituents are themselves optionally substituted by deuterium-, hydroxy-, amino-, trifluoromethyl-, cyano-, nitro-, carboxy-, ($C_1$–$C_4$)alkoxy-, ($C_1$–$C_6$)acyloxy-, ($C_1$–$C_6$)alkylamino-, (($C_1$–$C_6$)alkyl)$_2$amino-, ($C_1$–$C_6$)alkyl-($C_2$–$C_6$)alkenyl-, ($C_2$–$C_6$)alkynyl-, ($C_1$–$C_6$)acylamino-, ($C_3$–$C_{10}$)cycloalkyl-, ($C_3$–$C_{10}$) heterocycloalkyl-, cyano($C_1$–$C_6$)alkyl-, trifluoromethyl($C_1$–$C_6$)alkyl-, nitro($C_1$–$C_6$)alkyl-, and ($C_1$–$C_6$)acylamino; and $R^3$ represents one or more optional substituents on a ring carbon atom, including at X where X is —$CH_2$—, selected from the groups consisting of ($C_1$–$C_6$)alkyl-, trihalo($C_1$–$C_6$)alkyl-, deuterium, and fluorine.

2. A compound according to claim 1, wherein the structural component thereof that is represented by

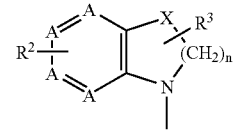

represents: 1,2,3,4-tetrahydroquinoline; 1,2,3,4-tetrahydroquinoxaline; 3,4-Dihydro-1H-quinoxaline-2-one; 3,4-Dihydro-2H-benzo[1,4]oxazine; 2,3-Dihydro-1H-indole; or 3,4-Dihydro-2H-benzo[1,4]thiazine.

3. A compound according to claim 2, wherein said structural component represents: 6-methoxy-1,2,3,4-tetrahydroquinoline; 4-methyl-1,2,3,4-tetrahydroquinoline; 7-(trifluoromethyl)-1,2,3,4-tetrahydroquinoline; 8-methyl-1,2,3,4-tetrahydroquinoline; 6-hydroxy-1,2,3,4-tetrahydroquinoline; 8-chloro-1,2,3,4-tetrahydroquinoline; 7-chloro-1,2,3,4-tetrahydroquinoline; 6-benzyloxy-7-methoxy-1,2,3,4-tetrahydroquinoline; 6,7-dimethyl-1,2,3,4-tetrahydroquinoxaline; 1,2,3,4-tetrahydroquinoxaline; 1-phenylsulfonyl-1,2,3,4-tetrahydroquinoxaline; 6-Methyl-1,2,3,4-Tetrahydroquinoline; 3,4-Dihydro-2H-benzo[1,4]oxazine; 5-Fluoro-2,3-dihydro-1H-indole; or 3,3-Dimethyl-2,3-dihydro-1H-indole.

4. A compound according to claim 1 wherein $R^1$ is 3,4,5-trimethoxyphenyl.

5. A compound according to claim 1 wherein one or more of substituents $R^2$ is selected from the groups consisting of (a) ($C_1$–$C_6$)alkyl-, ($C_1$–$C_6$)alkynl-, ($C_1$–$C_6$)alkoxy-, trihalo($C_1$–$C_6$)alkyl-, ($C_1$–$C_6$)alkylamino-, (($C_1$–$C_6$)$_2$) dialkylamino-, amino-, cyano, and halo-; and (b) benzyloxy-, phenylsulfonyl-, phenylaminocarbonyl-, ($C_1$–$C_9$)heteroarylsulfonyl-, and ($C_1$–$C_9$) heteroarylaminocarbonyl-, optionally substituted by one or more groups selected from the group consisting of ($C_1$–$C_6$)alkyl-, ($C_2$–$C_6$)alkynyl-, trihalo($C_1$–$C_6$) alkyl, ($C_1$–$C_6$)alkoxy-, ($C_1$–$C_6$)alkylamino-, (($C_1$–$C_6$)$_2$)alkylamino-, and halo.

6. A compound according to claim 1 wherein one or more of substituents $R^3$ is selected from the groups consisting of $(C_1-C_6)$alkyl-, trihalo$(C_1-C_6)$alkyl-, deuterium, and fluorine.

7. A compound according to claim 6 wherein $R^3$ is trifluoromethyl.

8. A compound selected from the group consisting of
   (a) 1-[(2-anilino)-4-pyrimidinyl]-6-methyl-1,2,3,4-tetrahydroquinoline;
   (b) 1-[2-[(4-bromophenyl)amino]-4-pyrimidinyl]-6-methyl-1,2,3,4-tetrahydroquinoline;
   (c) 1-[2-[(4-methoxyphenyl)amino]-4-pyrimidinyl]-6-methyl-1,2,3,4-tetrahydroquinoline;
   (d) 1-[2-[(1H-indazole-5-yl)]-4-pyrimidyl]-6-methyl-1,2,3,4-tetrahydroquinoline;
   (e) 1-[2-[(4-phenoxyphenyl)amino]-4-pyrimidinyl]-6-methyl-1,2,3,4-tetrahydroquinoline;
   (f) 1-[2-[(3,4-dimethoxyphenyl)amino]-4-pyrimidinyl]-6-methyl-1,2,3,4-tetrahydroquinoline;
   (g) 1-[2-[(3,4,5-trimethoxyphenyl)amino]-4-pyrimidinyl]-6-methyl-1,2,3,4-tetrahydroquinoline;
   (h) 1-[2-[(4,N-phenylaminophenyl)amino]-4-pyrimidinyl]-6-methyl-1,2,3,4-tetrahydroquinoline;
   (i) [4-(6-Methyl-3,4-dihydro-2H-quinolin-1-yl)-pyrimidin-2-yl]-(6-morpholin-4-yl-pyridin-3-yl)-amine;
   (j) 5-[4-(6-Methyl-3,4-dihydro-2H-quinolin-1-yl)-pyrimidin-2-ylamino]-1,3-dihydro-benzoimidazol-2-one;
   (k) (2,3-Dimethyl-1H-indol-5-yl)-[4-(6-methyl-3,4-dihydro-2H-quinolin-1-yl)-pyrimidin-2-yl]-amine;
   (l) [4-(6-Methyl-3,4-dihydro-2H-quinolin-1-yl)-pyrimidin-2-yl]-(2-methyl-2H-pyrazol-3-yl)-amine;
   (m) (6-Methoxy-pyridin-3-yl)-[4-(6-methyl-3,4-dihydro-2H-quinolin-1-yl )-pyrimidin-2-yl]-amine;
   (n) (4-Fluoro-3-methyl-phenyl)-[4-(6-methyl-3,4-dihydro-2H-quinolin-1-yl)-pyrimidin-2-yl]-amine;
   (o) (5-Cyclopropyl-2H-pyrazol-3-yl)-[4-(6-methyl-3,4-dihydro-2H-quinolin-1-yl)-pyrimidin-2-yl]-amine;
   (p) 4-Benzyl-N3-[4-(6-methyl-3,4-dihydro-2H-quinolin-1-yl)-pyrimidin-2-yl]-1H-pyrazole-3,5-diamine;
   (q) [4-(6-Methyl-3,4-dihydro-2H-quinolin-1-yl)-pyrimidin-2-yl]-(4-methyl-thiazol-2-yl)-amine; and
   (r) [4-(6-Methyl-3,4-dihydro-2H-quinolin-1-yl)-pyrimidin-2-yl]-(5-methyl-1H-pyrazol-3-yl)-amine.

9. A compound selected from the group consisting of
   (a) [4-(3,4-Dihydro-2H-quinolin-1-yl)-pyrimidin-2-yl]-(6-pyrrolidin-1-yl-pyridin-3-yl)-amine;
   (b) (1-Cyclopentyl-1H-indol-6-yl)-[4-(6-methyl-3,4-dihydro-2H-quinolin-1-yl)-pyrimidin-2-yl]-amine;
   (c) [4-(6-Methyl-3,4-dihydro-2H-quinolin-1-yl)-pyrimidin-2-yl]-oxazol-4-yl-amine;
   (d) (3,4-Dichloro-phenyl)-[4-(6-methyl-3,4-dihydro-2H-quinolin-1-yl)-pyrimidin-2-yl]-amine; and
   (e) [4-(3,4-Dihydro-2H-quinolin-1-yl)-pyrimidin-2-yl]-isothiazol-3-yl-amine.

10. A compound selected from the group consisting of
    (a) 2-({5-[4-(2,3-Dihydro-benzo[1,4]oxazin-4-yl)-pyrimidin-2-ylamino]-pyridin-2-yl}-methyl-amino)-ethanol;
    (b) N-{5-[4-(3-Oxo-3,4-dihydro-2H-quinoxalin-1-yl)-pyrimidin-2-ylamino]-pyridin-2-yl}-acetamide;
    (c) 3-Chloro-N-[4-(4-methyl-3-oxo-3,4-dihydro-2H-quinoxalin-1-yl)-pyrimidin-2-yl]-benzamide;
    (d) [4-(2,3-Dihydro-benzo[1,4]thiazin-4-yl)-pyrimidin-2-yl]-oxazol-4-yl-amine;
    (e) N-[4-(5-Fluoro-2,3-dihydro-indol-1-yl)-pyrimidin-2-yl]-3-methoxy-benzenesulfonamide;
    (f) [4-(5,6-Dihydro-pyrrolo[2,3-d]pyrimidin-7-yl)-pyrimidin-2-yl]-(2-trifluoromethyl-phenyl)-amine;
    (g) 6-Methoxy-1-[2-(pyridazin-3-ylamino)-pyrimidin-4-yl]-2,3-dihydro-1H-quinolin-4-one;
    (h) 2-{5-[4-(3,4-Dihydro-2H-quinoxalin-1-yl)-pyrimidin-2-ylamino]-indol-1-yl}-ethanol;
    (i) (2H-Pyrazol-3-yl)-[4-(7-trifluoromethyl-3,4-dihydro-2H-quinolin-1-yl)-pyrimidin-2-yl]-amine;
    (j) 1-[4-(3,4-Dihydro-2H-[1,5]naphthyridin-1-yl)-pyrimidin-2-yl]-3-ethyl-urea;
    (k) 1-[4-(2,3-Dihydro-benzo[1,4]oxazin-4-yl)-pyrimidin-2-yl]-3-(2-ethoxy-ethyl)-urea;
    (l) [4-(3,3-Dimethyl-2,3-dihydro-indol-1-yl)-pyrimidin-2-yl]-carbamic acid tert-butyl ester;
    (m) 3-Cyano-N-[4-(7-methoxy-2,3,4,5-tetrahydro-benzo[b]azepin-1-yl)-pyrimidin-2-yl]-benzamide;
    (n) Isoxazol-4-yl-[4-(2,3,4,5-tetrahydro-benzo[b][1,4]diazepin-1-yl)-pyrimidin-2-yl]-amine;
    (o) (3,4-Dichloro-phenyl)-[4-(3,4-dihydro-2H-benzo[b][1,4]thiazepin-5-yl)-pyrimidin-2-yl]-amine;
    (p) (6-Aziridin-1-yl-pyridin-3-yl)-[4-(5-methanesulfonyl-2,3-dihydro-indol-1-yl)-pyrimidin-2-yl]-amine;
    (q) $N^2$-Cyclopropyl-$N^5$-[4-(6-fluoro-3,4-dihydro-2H-quinolin-1-yl)-pyrimidin-2-yl]-pyridine-2,5-diamine; and
    (r) Benzo[1,3]dioxole-5-carboxylic acid [4-(6-fluoro-3,4-dihydro-2H-quinolin-1-yl)-pyrimidin-2-yl]-amide.

11. A compound according to claim 1, wherein X is methylene.

12. A compound according to claim 1, wherein the structural component thereof that is represented by

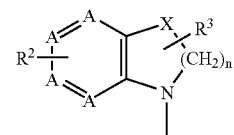

represents: 2,3-Dihydro-1H-pyrrolo[2,3-b]pyridine; 2,3-Dihydro-1H-pyrrolo[2,3-c]pyridine; 2,3-Dihydro-1H-pyrrolo[3,2-c]pyridine; 2,3-Dihydro-1H-pyrrolo[3,2-b]pyridine; 6,7-Dihydro-5H-pyrrolo[3,2-d]pyrimidine; 6,7-Dihydro-5H-pyrrolo[3,2-d][1,2,3]triazine; 6,7-Dihydro-5H-pyrrolo[2,3-d][1,2,3]triazine; 1,4,5,7-Tetraaza-indan; 1,4,6,7-Tetraaza-indan; 6,7-Dihydro-5H-pyrrolo[2,3-c]pyridazine; 2,3-Dihydro-1H-pyrrolo[2,3-d]pyridazine; 6,7-Dihydro-5H-pyrrolo[3,2-c]pyridazine; 6,7-Dihydro-5H-pyrrolo[2,3-b]pyrazine; 6,7-Dihydro-5H-pyrimido[4,5-b][1,4]oxazine; 5,6,7,8-Tetrahydro-pteridine; 1,2,3,4-Tetrahydro-pyrido[2,3-b]pyrazine; 1,2,3,4-Tetrahydro-pyrido[3,4-b]pyrazine; 1,2,3,4-Tetrahydro-pyrido[3,4-b]pyrazine; 1,2,3,4-Tetrahydro-pyrido[2,3-b]pyrazine; 5,6,7,8-Tetrahydro-pyrazino[2,3-c]pyridazine; 5,6,7,8-Tetrahydro-pteridine; 1,2,3,4-Tetrahydro-pyrazino[2,3-d]pyridazine; 5,6,7,8-Tetrahydro-pyrazino[2,3-c]pyridazine; 1,2,3,4-Tetrahydro-pyrazino[2,3-b]pyrazine; 5,6,7,8-Tetrahydro-pyrazino[2,3-e][1,2,4]triazine; 5,6,7,8-Tetrahydro-pyrazino[2,3-e][1,2,4]triazine; 5,6,7,8-

Tetrahydro-pyrazino[2,3-d][1,2,3]triazine; 5,6,7,8-Tetrahydro-pyrazino[2,3-d][1,2,3]triazine; 2,3-Dihydro-1H-4-oxa-1,5-diaza-naphthalene; 2,3-Dihydro-1H-4-oxa-1,6-diaza-naphthalene; 3,4-Dihydro-2H-1-oxa-4,6-diaza-naphthalene; 3,4-Dihydro-2H-1-oxa-4,5-diaza-naphthalene; 7,8-Dihydro-6H-5-oxa-1,2,8-triaza-naphthalene; 3,4-Dihydro-2H-1-oxa-4,6,7-triaza-naphthalene; 6,7-Dihydro-5H-8-oxa-1,2,5-triaza-naphthalene; 3,4-Dihydro-2H-1-oxa-4,5,8-triaza-naphthalene; 7,8-Dihydro-6H-pyrimido[5,4-b][1,4]oxazine; 6,7-Dihydro-5H-pyrimido[4,5-b][1,4]oxazine; 6,7-Dihydro-5H-8-oxa-1,2,3,5-tetraaza-naphthalene; 6,7-Dihydro-5H-8-oxa-1,2,4,5-tetraaza-naphthalene; 7,8-Dihydro-6H-5-oxa-1,2,3,8-tetraaza-naphthalene; 6,7-Dihydro-5H-8-oxa-1,2,4,5-tetraaza-naphthalene; 2,3-Dihydro-1H-pyrido[2,3-b][1,4]thiazine; 2,3-Dihydro-1H-4-thia-1,6-diaza-naphthalene; 3,4-Dihydro-2H-1-thia-4,6-diaza-naphthalene; 3,4-Dihydro-2H-pyrido[3,2-b][1,4]thiazine; 7,8-Dihydro-6H-5-thia-1,2,8-triaza-naphthalene; 3,4-Dihydro-2H-1-thia-4,6,7-triaza-naphthalene; 6,7-Dihydro-5H-8-thia-1,2,5-triaza-naphthalene; 6,7-Dihydro-5H-pyrimido[4,5-b][1,4]thiazine; 7,8-Dihydro-6H-pyrimido[5,4-b][1,4]thiazine; 3,4-Dihydro-2H-1-thia-4,5,8-triaza-naphthalene; 6,7-Dihydro-5H-8-thia-1,2,4,5-tetraaza-naphthalene; 7,8-Dihydro-6H-5-thia-1,2,4,8-tetraaza-naphthalene; 7,8-Dihydro-6H-5-thia-1,2,3,8-tetraaza-naphthalene; 6,7-Dihydro-5H-8-thia-1,2,3,5-tetraaza-naphthalene; 5,6,7,8-Tetrahydro-pyrido[3,2-d]pyrimidine; 1,2,3,4-Tetrahydro-pyrido[2,3-d]pyridazine; 5,6,7,8-Tetrahydro-pyrido[2,3-b]pyrazine; 5,6,7,8-Tetrahydro-pyrido[3,2-e][1,2,4]triazine; 5,6,7,8-Tetrahydro-pyrido[2,3-e][1,2,4]triazine; 5,6,7,8-Tetrahydro-pyrido[3,2-d][1,2,3]triazine; or 5,6,7,8-Tetrahydro-pyrido(2,3-d][1,2,3]triazine.

13. A pharmaceutical composition comprising an effective amount of a compound according to claim 1, and a pharmaceutical carrier.

* * * * *